United States Patent [19]

Baker et al.

[11] Patent Number: 5,576,319
[45] Date of Patent: Nov. 19, 1996

[54] PYRROLO-PYRIDINE DERIVATIVES

[75] Inventors: Raymond Baker, Green Tye; Janusz J. Kulagowski, Bishops Stortford; Neil R. Curtis, Puckeridge; Paul D. Leeson, Cambridge; Mark P. Ridgill, Watton-At-Stone; Adrian L. Smith, Bishops Stortford, all of England

[73] Assignee: Merck, Sharp & Dohme Ltd., Hoddesdon, England

[21] Appl. No.: 296,574

[22] Filed: Aug. 26, 1994

[51] Int. Cl.$^6$ ............... A61K 31/495; C07D 401/02; C07D 241/02; C07D 403/02
[52] U.S. Cl. ............ 514/253; 514/254; 544/121; 544/296; 544/357; 544/362; 544/363
[58] Field of Search ............... 544/362, 363, 544/121, 296, 357, 362, 363; 514/253, 254

[56] References Cited

U.S. PATENT DOCUMENTS 3,362,956  1/1968  Archer ..................... 514/253
3,511,841  5/1970  Archer ..................... 514/253

FOREIGN PATENT DOCUMENTS

WO92/10571  6/1992  WIPO.

OTHER PUBLICATIONS

Goodman and Gilman's, The Pharmacological Basis of Therapeutics, 8th Edition, pp. 386–387 (1980).

The Merck Index, 9th Edition, 1976, entries 2176 and 4450.

"Cloning of the gene for a human dopamine D4 receptor with high affinity for the antipsychotic clozapine", Hubert H. M. Van Tol, et al., Nature, vol. 350, Apr. 18, 1991, pp. 610–614.

"Cloning of the gene for a human dopamine D5 receptor with higher affinity for dopamine than D1", Roger K. Sunahara, et al., Nature, vol. 350, Apr. 18, 1991, pp. 614–619.

Primary Examiner—Cecilia Tsang
Attorney, Agent, or Firm—Robert J. North; Melvin Winokur

[57] ABSTRACT

A class of pyrrolo[2,3-b]pyridine derivatives, substituted at the 3-position by a substituted piperazinylmethyl moiety, are antagonists of dopamine receptor subtypes within the brain, having a selective affinity for the dopamine $D_4$ receptor subtype over other dopamine receptor subtypes, and are accordingly of benefit in the treatment and/or prevention of psychotic disorders such as schizophrenia whilst manifesting fewer side-effects than those associated with classical neuroleptic drugs.

30 Claims, No Drawings

PYRROLO-PYRIDINE DERIVATIVES

This invention relates to the use of a particular class of heteroaromatic compounds. More particularly, the invention is concerned with the use of substituted pyrrolo[2,3-b] pyridine derivatives which are antagonists of dopamine receptor subtypes within the brain and are therefore of benefit in the treatment and/or prevention of psychotic disorders such as schizophrenia.

The "dopamine hypothesis" of schizophrenia predicts an increased activity of dopamine neurotransmission in the disease. The hypothesis is supported by early observations that drugs, such as amphetamine, with dopamine agonist or dopamine-releasing properties are capable of eliciting a psychosis indistinguishable from acute paranoid schizophrenia.

Schizophrenia is a disorder which is conventionally treated with drugs known as neuroleptics. In the majority of cases, the symptoms of schizophrenia can be treated successfully with so-called "classical" neuroleptic agents such as haloperidol. Classical neuroleptics generally are antagonists at dopamine $D_2$ receptors. The fact that classical neuroleptic drugs have an action on dopamine receptors in the brain thus lends credence to the "dopamine hypothesis" of schizophrenia.

Molecular biological techniques have revealed the existence of several subtypes of the dopamine receptor. The dopamine $D_1$ receptor subtype has been shown to occur in at least two discrete forms. Two forms of the $D_2$ receptor subtype, and at least one form of the $D_3$ receptor subtype, have also been discovered. More recently, the $D_4$ (Van Tol et al., *Nature* (London), 1991, 350, 610) and $D_5$ (Sunahara et al., *Nature* (London), 1991, 350, 614) receptor subtypes have been described.

Notwithstanding their beneficial antipsychotic effects, classical neuroleptic agents such as haloperidol are frequently responsible for eliciting extrapyramidal symptoms (movement disorders) and neuroendocrine (hormonal) disturbances. These side-effects, which clearly detract from the clinical desirability of classical neuroleptics, are believed to be attributable to $D_2$ receptor blockade in the striatal region of the brain. It is considered (Van Tol et al., supra; and WO-A-92/10571) that compounds which can interact selectively with the dopamine $D_4$ receptor subtype, whilst having a less-pronounced action at the $D_2$ subtype, might be free from, or at any rate less prone to, the side-effects associated with classical neuroleptics, whilst at the same time maintaining a beneficial level of antipsychotic activity.

The compounds of use in the present invention, being antagonists of dopamine receptor subtypes within the brain, are accordingly of benefit in the treatment and/or prevention of psychotic disorders such as schizophrenia. In particular, the compounds of use in this invention are extremely potent antagonists of the human dopamine $D_4$ receptor subtype. Moreover, the compounds of use in the invention have a selective affinity for the dopamine $D_4$ receptor subtype over other dopamine receptor subtypes, in particular the $D_2$ subtype, and can therefore be expected to manifest fewer side-effects than those associated with classical neuroleptic drugs.

U.S. Pat. Nos. 3,362,956 and 3,511,841 describe certain 1-[(heterocyclyl)-lower-alkyl]-4-substituted piperazines, in which the heterocyclyl moiety represents inter alia a pyrrolo [2,3-b]pyridine group (referred to therein as a 7-azaindole group). These compounds are alleged therein to possess a panopyl of depressant actions on the automatic nervous system, the cardiovascular system and the skeletal muscular system (including psychomotor depressant, sedative, adrenolytic, rectal temperature lowering, anticonvulsant, blood pressure lowering and heart force increasing activities), and are consequently alleged to be useful as tranquilizers, sedatives, adrenolytic agents, hypothermic agents, anti-convulsants, hypotensive agents and cardiovascular agents. There is, however, no teaching in U.S. Pat. Nos. 3,362,956 or 3,511,841 that the compounds described therein would be of any benefit in the treatment and/or prevention of psychotic disorders such as schizophrenia, still less that in doing so they might be expected to manifest fewer side-effects than those exhibited by classical neuroleptic agents. In addition, pronounced adrenolytic activity, hypothermic activity, hypotensive activity and cardiovascular activity would be considered unwanted side-effects for a medicament to be used for the treatment of schizophrenia.

In particular, the compounds in U.S. Pat. Nos. 3,362,956 and 3,511,841 are stated to be useful in inter alia tranquilizers and sedatives. However, a purely tranquilizing or sedative agent would merely subdue the schizophrenic patient without integrating the behaviour. An objective of the present invention is to help restore an essentially "normal" lifestyle to the schizophrenic patient whilst subduing the patient as little as possible.

The present invention accordingly provides a method of alleviating the symptoms of schizophrenia without causing sedation or extrapyramidal side-effects, which method comprises administering to a patient in need of such treatment a therapeutically effective amount of a compound of formula I, or a pharmaceutically acceptable salt thereof or a prodrug thereof:

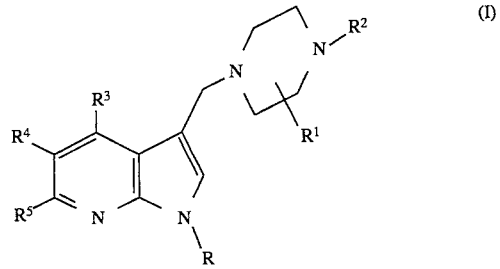

wherein

R represents hydrogen or $C_{1-6}$ alkyl;

$R^1$ represents hydrogen, halogen, or an optionally substituted $C_{1-6}$ alkyl, $C_{1-6}$ alkoxy, $C_{2-6}$ alkenyl, $C_{2-6}$ alkynyl, aryl, aryl($C_{1-6}$) alkyl, aryloxy($C_{1-6}$)alkyl, aryl($C_{1-6}$)alkoxy, aryl($C_{2-6}$)alkenyl, aryl($C_{2-6}$)alkynyl, $C_{3-7}$ heterocycloalkyl($C_{1-6}$)alkyl, heteroaryl, heteroaryl($C_{1-6}$)alkyl, heteroaryl($C_{2-6}$)alkenyl or heteroaryl($C_{2-6}$)alkynyl group; or $R^1$ represents a straight or branched alkylene chain containing from 1 to 4 carbon atoms, and optionally incorporating an oxygen atom, which links the piperazine moiety to the group $R^2$;

$R^2$ represents an optionally substituted $C_{1-6}$ alkyl $C_{1-6}$ alkoxy, $C_{2-6}$ alkenyl, $C_{2-6}$ alkynyl, aryl, aryl($C_{1-6}$)alkyl, aryloxy($C_{1-6}$)alkyl, aryl($C_{1-6}$)alkoxy, aryl($C_{2-6}$)alkenyl, aryl($C_{2-6}$)alkynyl, $C_{3-7}$ heterocycloalkyl($C_{1-6}$)alkyl, heteroaryl, heteroaryl($C_{1-6}$)alkyl, heteroaryl($C_{2-6}$)alkenyl or heteroaryl($C_{2-6}$)alkynyl group;

$R^3$, $R^4$ and $R^5$ independently represent hydrogen, hydrocarbon, a heterocyclic group, halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$ or —$CONR^aR^B$; and $R^a$ and $R^b$ independently represent hydrogen, hydrocarbon or a heterocyclic group.

Aptly, a compound of formula I or a pharmaceutically acceptable salt thereof is employed in the method of this invention.

As will be appreciated, the method according to the invention alleviates the symptoms of schizophrenia, but does not cause sedation or extrapyramidal disorders at the dose of the compound of formula I which is therapeutically effective in alleviating the symptoms of schizophrenia.

Also of use in the method according to the present invention invention are the compounds of formula I above wherein $R^1$ is other than a straight or branched alkylene chain containing from 1 to 4 carbon atoms, and optionally incorporating an oxygen atom, which links the piperazine moiety to the group $R^2$; and the remaining substituents are as defined with reference to formula I above.

Most aptly, a compound of formula I or a pharmaceutically acceptable salt thereof is employed in the method of this invention.

In another aspect, the invention provides a method for the treatment and/or prevention of psychotic disorders, such as schizophrenia, which method comprises administering to a patient in need of such treatment an effective amount of a compound of formula I, as defined above, or a pharmaceutically acceptable salt thereof or a prodrug thereof. Aptly, a compound of formula I or a pharmaceutically acceptable salt thereof is employed in the method of this invention.

The symptoms of schizophrenia are conventionally divided into two sub-classes, namely the so-called "positive" and "negative" symptoms. The positive symptoms of schizophrenia are characterized by florid thought disorders and hallucinations. The negative symptoms of schizophrenia, meanwhile, are characterized by a "blunting of affect"; in other words, the patient manifests a passive or low-key response in circumstances where a more active response is warranted.

In one embodiment, therefore, the method according to the invention is directed towards alleviating the positive symptoms of schizophrenia. In another embodiment, meanwhile, the method according to the invention is directed towards alleviating the negative symptoms of schizophrenia.

In order to elicit their advantageous properties, the compounds of use in this invention ideally have a human dopamine $D_4$ receptor subtype binding affinity ($K_i$) of 10 nm or less, preferably 2 nm or less; and at least a 50-fold, more aptly at least a 70-fold, preferably at least a 100-fold, more preferably at least 250-fold, and most preferably at least a 500-fold, selective affinity for the $D_4$ subtype with respect to the $D_2$ subtype (i.e. the $K_i$ values for $D_4$ are correspondingly lower than those for $D_2$ in the stated ratios).

For use in medicine, the salts of the compounds of formula I will be pharmaceutically acceptable salts. Other salts may, however, be useful in the preparation of the compounds of use in the invention or of their pharmaceutically acceptable salts. Suitable pharmaceutically acceptable salts of the compounds of use in this invention include acid addition salts which may, for example, be formed by mixing a solution of the compound of use in the invention with a solution of a pharmaceutically acceptable acid such as hydrochloric acid, sulphuric acid, fumaric acid, maleic acid, succinic acid, acetic acid, benzoic acid, oxalic acid, citric acid, tartaric acid, carbonic acid or phosphoric acid. Furthermore, where the compounds of use in the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl, aryl($C_{1-6}$)alkyl, aryl($C_{2-6}$)alkenyl and aryl($C_{2-6}$)alkynyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include $C_{3-7}$ heterocycloalkyl, $C_{3-7}$ heterocycloalkyl($C_{1-6}$)alkyl, heteroaryl, heteroaryl($C_{1-6}$)alkyl, heteroaryl($C_{2-6}$)alkenyl and heteroaryl($C_{2-6}$)alkynyl groups.

Suitable alkyl groups within the scope of the term "hydrocarbon" and within the definition of the substituents R, $R^1$ and $R^2$ include straight-chained and branched alkyl groups containing from 1 to 6 carbon atoms. Typical examples include methyl and ethyl groups, and straight-chained or branched propyl and butyl groups. Particular alkyl groups are methyl, ethyl, n-propyl, isopropyl and t-butyl.

Suitable alkenyl groups within the scope of the term "hydrocarbon" and within the definitions of the substituents $R^1$ and $R^2$ include straight-chained and branched alkenyl groups containing from 2 to 6 carbon atoms. Typical examples include vinyl and allyl groups.

Suitable alkynyl groups within the scope of the term "hydrocarbon" and within the definition of the substituents $R^1$ and $R^2$ include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Particular aryl groups within the scope of the term "hydrocarbon" and within the definition of the substituents $R^1$ and $R^2$ include phenyl and naphthyl.

Particular aryl($C_{1-6}$)alkyl groups within the scope of the term "hydrocarbon" and within the definition of the substituents $R^1$ and $R^2$ include benzyl, naphthylmethyl, phenethyl and phenylpropyl.

Suitable heterocycloalkyl groups include azetidinyl, pyrrolidyl, piperidyl, piperazinyl, morpholinyl and tetrahydrofuryl groups.

A particular $C_{3-7}$ heterocycloalkyl($C_{1-6}$)alkyl group within the scope of the expression "a heterocyclic group" and within the definition of the substituents $R^1$ and $R^2$ is tetrahydrofurylethyl.

Suitable heteroaryl groups within the scope of the expression "a heterocyclic group" and within the definition of the substituents $R^1$ and $R^2$ include pyridyl, quinolyl, isoquinolyl, pyridazinyl, pyrimidinyl, pyrazinyl, pyranyl, furyl, benzofuryl, dibenzofuryl, thienyl, benzthienyl, indolyl, indazolyl, imidazolyl, benzimidazolyl, oxadiazolyl and thiadiazolyl groups.

Particular heteroaryl ($C_{1-6}$)alkyl groups within the scope of the expression "a heterocyclic group" and within the definition of the substituents $R^1$ and $R^2$ include thienylmethyl, pyridylmethyl, pyrimidinylmethyl and pyrazinylmethyl.

The hydrocarbon and heterocyclic groups, as well as the substituents $R^1$ and $R^2$, may in turn be optionally substituted by one or more groups selected from $C_{1-6}$ alkyl, adamantyl, phenyl, aryl($C_{1-6}$)alkyl, halogen, halo($C_{1-6}$)alkyl, amino ($C_{1-6}$)alkyl, $C_{1-6}$ alkylamino($C_{1-6}$)alkyl, di($C_{1-6}$)alkylamino($C_{1-6}$)alkyl, trifluoromethyl, hydroxy, hydroxy($C_{1-6}$)alkyl, $C_{1-6}$ alkoxy, $C_{1-6}$ alkoxy($C_{1-6}$)alkyl, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, arylcarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, trifluoroemthanesulphonyloxy, —NR$^v$R$^w$, —NR$^v$COR$^w$, —NR$^v$CO$_2$R$^w$, —NR$^v$SO$_2$R$^w$, —CH$_2$NR$^v$SO$_2$R$^w$, —NHCONR$^v$R$^w$, —PO(OR$^v$)(OR$^w$), —CONR$^v$R$^w$, —SO$_2$NR$^v$R$^w$ and —CH$_2$SO$_2$NR$^v$R$^w$, in which R$^v$ and R$^w$ independently represent hydrogen, $C_{1-6}$ alkyl, aryl or aryl($C_{1-6}$)alkyl.

The term "halogen" as used herein includes fluorine, chlorine, bromine and iodine, especially chlorine.

The present invention includes within its scope the use of prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in "Design of Prodrugs", ed. H. Bundgaard, Elsevier, 1985.

Where the compounds of use in the invention have at least one asymmetric centre, they may accordingly exist as enantiomers. Where the compounds of use in the invention possess two or more asymmetric centres, they may additionally exist as diastereoisomers. It is to be understood that the use of all such isomers and mixtures thereof is encompassed within the scope of the present invention.

Suitably, the substituents R represents hydrogen or methyl, especially hydrogen.

Suitably, the substituents R$^1$ represents hydrogen, fluoro or chloro, especially hydrogen.

When R$^1$ represents a straight or branched alkylene chain containing from 1 to 4 carbon atoms, and optionally incorporating an oxygen atom, which links the piperazine moiety to the group R$^2$, this suitably a methylene, ethylene or oxamethylene chain.

Suitable values for the substituent R$^2$ include $C_{1-6}$ alkyl, aryl, aryl($C_{1-6}$)alkyl, aryloxy($C_{1-6}$)alkyl and heteroaryl, any of which groups may be optionally substituted. Preferred values of R$^2$ include aryl, aryl($C_{1-6}$)alkyl, aryloxy($C_{1-6}$)alkyl and heteroaryl, any of which groups may be optionally substituted. In a particularly preferred embodiment, R$^2$ represents an optionally substituted aryl group, in particular an optionally substituted phenyl group.

Examples of optional substituents on the group R$^2$ include $C_{1-6}$ alkyl, halogen, trifluoromethyl, hydroxy, hydroxy($C_{1-6}$)alkyl, $C_{1-6}$ alkoxy, $C_{1-6}$ alkoxy($C_{1-6}$)alkyl, $C_{1-3}$ alkylenedioxy, carboxy, $C_{2-6}$ alkoxycarbonyl, nitro, $C_{1-6}$ alkylamino, di($C_{1-6}$)alkylamino, $C_{1-6}$ alkylamino($C_{1-6}$)alkyl and di($C_{1-6}$)alkylamino($C_{1-6}$)alkyl.

Particular values of R$^2$ include methyl, ethyl, n-propyl, isopropyl, phenyl, methylphenyl, ethylphenyl, fluorophenyl, chlorophenyl, dichlorophenyl, bromophenyl, iodophenyl, trifluoromethyl-phenyl, hydroxyphenyl, hydroxymethyl-phenyl, methoxyphenyl, ethoxyphenyl, methoxymethyl-phenyl, methylenedioxy-phenyl, carboxyphenyl, methoxycarbonyl-phenyl, ethoxycarbonyl-phenyl, nitrophenyl, dimethylamino-phenyl, dimethylaminomethyl-phenyl, benzyl, chlorobenzyl, phenethyl, phenoxy-ethyl, methylpyridyl, chloropyridyl, isoquinolyl, indolyl, methylinodolyl, indazolyl and benzthienyl.

More particular values of R$^2$ include phenyl, methylphenyl, ethylphenyl, fluorophenyl, chlorophenyl, dichlorophenyl, bromophenyl, iodophenyl, trifluoromethylphenyl, hydroxyphenyl, hydroxymethyl-phenyl, methoxyphenyl, ethoxyphenyl, methoxymethyl-phenyl, methylenedioxyphenyl, carboxyphenyl, methoxycarbonyl-phenyl, ethoxycarbonyl-phenyl, dimethylamino-phenyl, dimethylaminomethyl-phenyl, benzyl, phenoxy-ethyl, methylpyridyl, chloropyridyl, isoquinolyl, indolyl, methylindolyl, indazolyl and benzthienyl.

A most particular value of R$^2$ is chlorophenyl.

Suitable values for the substituents R$^3$, R$^4$ and R$^5$ include hydrogen, halogen, cyano, nitro, trifluoromethyl, amino, $C_{1-6}$ alkylamino, di($C_{1-6}$)alkylamino, $C_{1-6}$ alkyl, $C_{1-6}$ alkoxy, aryl($C_{1-6}$)alkoxy and $C_{2-6}$ alkylcarbonyl. Particular values include hydrogen, fluoro, chloro, methyl, methoxy and benzyloxy, especially hydrogen.

A particular sub-class of compounds of use in the invention is represented by the compounds of formula IIA, and pharmaceutically acceptable salts thereof and prodrugs thereof:

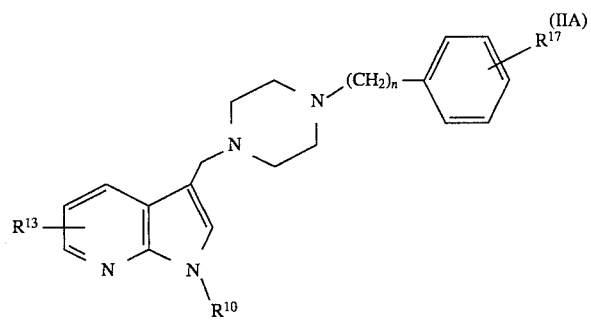

(IIA)

wherein n is zero, 1, 2 or 3;

R$^{10}$ represents hydrogen or methyl, especially hydrogen;

R$^{13}$ represents hydrogen, halogen, cyano, nitro, trifluoromethyl, amino, $C_{1-6}$ alkylamino, di($C_{1-6}$)alkylamino, $C_{1-6}$ alkyl, $C_{1-6}$ alkoxy, aryl($C_{1-6}$)alkoxy or $C_{2-6}$ alkylcarbonyl; and R$^{17}$ represents hydrogen, $C_{1-6}$ alkyl, halogen, trifluoromethyl, hydroxy, hydroxy($C_{1-6}$)alkyl, $C_{1-6}$ alkoxy, aryl($C_{1-6}$)alkoxy, $C_{1-6}$ alkoxy($C_{1-6}$)alkyl, carboxy, $C_{2-6}$ alkoxycarbonyl, $C_{2-6}$ alkylcarbonyl, cyano, nitro, amino, $C_{1-6}$ alkylamino, di($C_{1-6}$)alkylamino, amino($C_{1-6}$)alkyl, $C_{1-6}$ alkylamino($C_{1-6}$)alkyl or di($C_{1-6}$) alkylamino($C_{1-6}$)alkyl.

Suitably, n is zero or 1, especially zero.

Particular values of R$^{13}$ include hydrogen, fluoro, chloro, methyl, ethyl, methoxy and benzyloxy, especially hydrogen.

Particular values of R$^{17}$ include hydrogen, methyl, ethyl, fluoro, chloro, bromo, iodo, trifluoromethyl, hydroxy, hydroxymethyl, methoxy, ethoxy, methoxymethyl, carboxy, methoxycarbonyl, ethoxycarbonyl, nitro, dimethylamino and dimethylaminomethyl.

Another sub-class of compounds of use in the invention is represented by the compounds of formula IIB, and pharmaceutically acceptable salts thereof and prodrugs thereof:

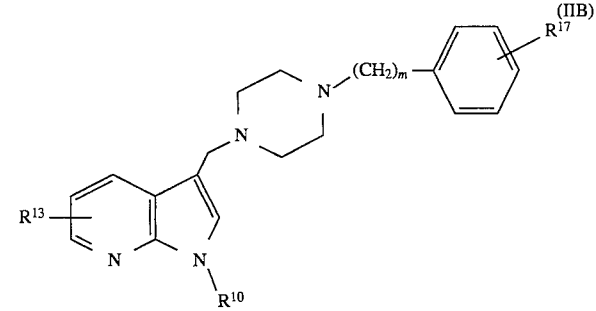

(IIB)

wherein m is 1, 2 or 3; and $R^{10}$, $R^{13}$ and $R^{17}$ are as defined with reference to formula IIA above.

A further sub-class of compounds of use in the invention is represented by the compounds of formula IIC, and pharmaceutically acceptable salts thereof and prodrugs thereof:

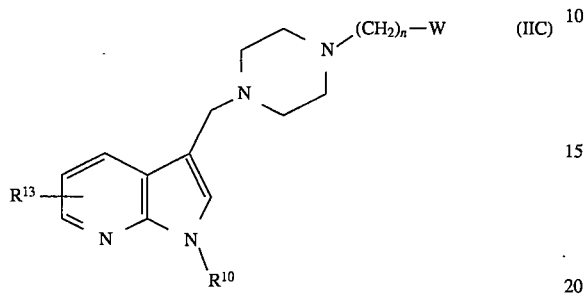

wherein n, $R^{10}$ and $R^{13}$ are as defined with reference to formula IIA above; and W represents a group of formula (i), (ii), (iii) or (iv):

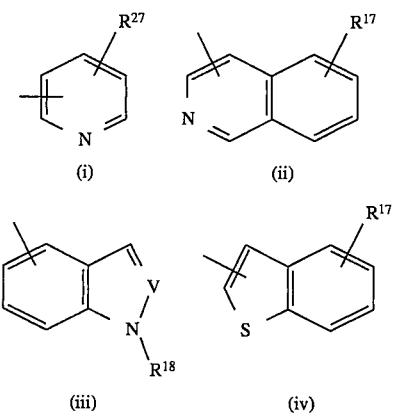

in which

V represents nitrogen or CH;

$R^{17}$ is as defined with reference to formula IIA above;

$R^{18}$ represents hydrogen or methyl; and $R^{27}$ represents $C_{1-6}$ alkyl, halogen, trifluoromethyl, $C_{1-6}$ alkoxy, cyano, nitro, amino, $C_{1-6}$ alkylamino or di($C_{1-6}$)alkylamino.

Suitably, $R^{27}$ is $C_{1-6}$ alkyl or halogen, especially methyl or chloro.

A still further sub-class of compounds of use in the invention is represented by the compounds of formula IID, and pharmaceutically acceptable salts thereof and prodrugs thereof:

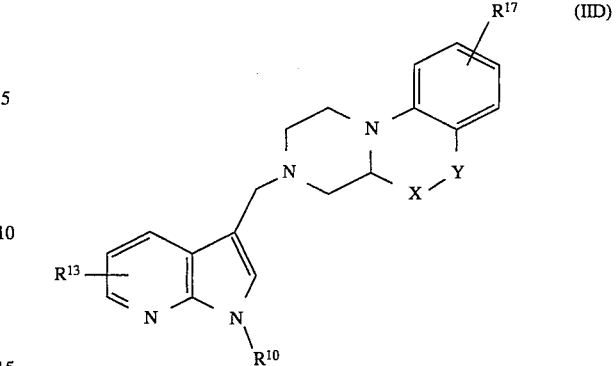

wherein

X represents a group of formula —$CH_2$— or —$CH_2CH_2$—;

Y represents a chemical bond or an oxygen atom; and $R^{10}$, $R^{13}$ and $R^{17}$ are as defined with reference to formula IIA above.

Certain compounds falling within the scope of formula I above are novel. Particular sub-classes of novel compounds in accordance with the present invention comprise the compounds of formula IIB, IIC and IID as defined above, and salts and prodrugs thereof. A discrete sub-class of novel compounds according to the invention comprises the compounds of formula IIE, and salts and prodrugs thereof:

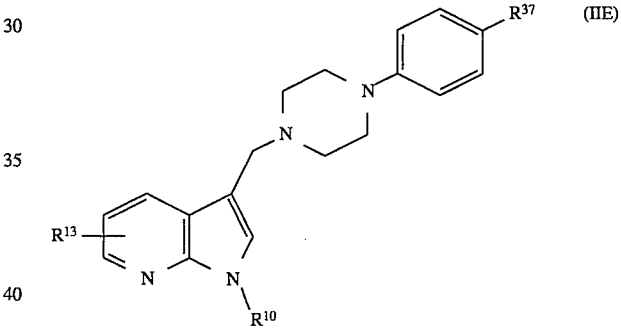

wherein $R^{13}$ is as defined with reference to formula IIA above; and $R^{37}$ represents fluoro, chloro, bromo, iodo or trifluoromethyl.

The compounds of formula IIE as defined above, and pharmaceutically acceptable salts thereof, have particularly advantageous properties as extremely potent antagonists of the human dopamine $D_4$ receptor subtype, and as selective antagonists of the dopamine $D_4$ receptor subtype relative to the $D_2$ subtype. They are therefore of use as agents for the treatment and/or prevention of psychotic disorders such as schizophrenia with manifestation of fewer side-effects than those associated with classical neuroleptic drugs. In particular, by virtue of these properties, the compounds of formula IIE as defined above, and pharmaceutically acceptable salts thereof, are especially effective in alleviating the symptoms of schizophrenia, especially the positive symptoms of schizophrenia, without causing sedation or extrapyramidal side-effects. The compounds may also be administered to patients who exhibit the negative symptoms of schizophrenia without causing sedation or extrapyramidal side-effects. These compounds of formula IIE will not, at the dose administered to effect human dopamine $D_4$ receptor subtype blockade, produce unacceptable side-affects due to cardiovascular activity.

The invention further provides a novel compound selected from the following:

3-(4-phenylpiperazin-1-yl)methyl-1H-pyrrolo[2,3-b]pyridine;
3-[4-(4-methoxyphenyl)piperazin-1-yl]methyl-1H-pyrrolo[2,3-b]pyridine;
3-(4-benzylpiperazin-1-yl)methyl-1H-pyrrolo[2,3-b]pyridine;
3-[4-(4-ethylphenyl)piperazin-1-yl]methyl-1H-pyrrolo[2,3-b]pyridine;
3-[4-(4-chlorophenyl)piperazin-1-yl]methyl-1H-pyrrolo[2,3-b]pyridine;
3-[4-(4-ethoxyphenyl)piperazin-1-yl]methyl-1H-pyrrolo[2,3-b]pyridine;
3-[4-(4-dimethylaminophenyl)piperazin-1-yl]methyl-1H-pyrrolo[2,3-b]pyridine;
3-[4-(3,4-dichlorophenyl)piperazin-1-yl]methyl-1H-pyrrolo[2,3-b]pyridine;
3-[4-(4-methoxyphenyl)piperazin-1-yl]methyl-1-methyl-1H-pyrrolo[2,3-b]pyridine;
3-[4-(5-chloropyrid-2-yl)piperazin-1-yl]methyl-1H-pyrrolo[2,3-b]pyridine;
3-[4-(3-isoquinolyl)piperazin-1-yl]methyl-1H-pyrrolo[2,3-b]pyridine;
3-[4-(5-indolyl)piperazin-1-yl]methyl-1H-pyrrolo[2,3-b]pyridine;
3-[4-(4-iodophenyl)piperazin-1-yl]methyl-1H-pyrrolo[2,3-b]pyridine;
3-[4-(4-trifluoromethylphenyl)piperazin-1-yl]methyl-1H-pyrrolo[2,3-b]pyridine;
3-[4-(2-phenoxyethyl)piperazin-1-yl]methyl-1H-pyrrolo[2,3-b]pyridine;
3-[4-(4-methylphenyl)piperazin-1-yl]methyl-1H-pyrrolo[2,3-b]pyridine;
3-[4-(4-fluorophenyl)piperazin-1-yl]methyl-1H-pyrrolo[2,3-b]pyridine;
3-[4-(1-methylindol-5-yl)piperazin-1yl]methyl-1H-pyrrolo[2,3-b]pyridine;
3-[4-(indazol-5-yl)piperazin-1-yl]methyl-1H-pyrrolo[2,3-b]pyridine;
3-[4-(4-ethoxycarbonylphenyl)piperazin-1yl]methyl-1H-pyrrolo[2,3-b]pyridine;
3-[4-(4-carboxyphenyl)piperazin-1-yl]methyl-1H-pyrrolo[2,3-b]pyridine;
3-[4-(3-methylphenyl)piperazin-1-yl]methyl-1H-pyrrolo[2,3-b]pyridine;
3-[4-(3,4-methylenedioxyphenyl)piperazin-1-yl]methyl-1H-pyrrolo[2,3-b]pyridine;
3-[4-(4-bromophenyl)piperazin-1-yl]methyl-1H-pyrrolo[2,3-b]pyridine;
3-[4-(4-methoxycarbonylphenyl)piperazin-1-yl]methyl-1H-pyrrolo[2,3-b]pyridine;
3-[4-(4-hydroxymethylphenyl)piperazin-1-yl]methyl-1H-pyrrolo[2,3-b]pyridine;
3-[4-(5-methylpyrid-2-yl)piperazin-1-yl]methyl-1H-pyrrolo[2,3-b]pyridine;
3-[4-(4-hydroxyphenyl)piperazin-1-yl]methyl-1H-pyrrolo[2,3-b]pyridine;
3-[4-(benzothiophen-2-yl)piperazin-1-yl]methyl-1H-pyrrolo[2,3-b]pyridine;
3-[4-(benzothiophen-3-yl)piperazin-1-yl]methyl-1H-pyrrolo[2,3-b]pyridine;
3-[(1H-pyrrolo[2,3-b]pyridine-3-yl)methyl]-2,3,4,4a,5,6-hexahydro-1(H)-pyrazino[1,2-a]quinoline;
8-chloro-3-[(1H-pyrrolo[2,3-b]pyridin-3-yl)methyl]-2,3,4,4a,5,6-hexahydro-1(H)-pyrazino[1,2-a]quinoline;
8-chloro-3-[(1H-pyrrolo[2,3-b]pyridin-3-yl)methyl]-2,3,4,4a,5,6-hexahydro-1(H)-pyrazino[2,3-c]-1,4-benzoxazine;
3-[4-(4-methoxymethylphenyl)piperazin-1-yl]methyl-1H-pyrrolo[2,3-b]pyridine;
3-[4-(4-dimethylaminomethylphenyl)piperazin-1-yl]methyl-1H-pyrrolo[2,3-b]pyridine;
3-(1,2,3,4,10,10a-hexahydropyrazino[1,2-a]indol-2-yl)methyl-1H-pyrrolo[2,3-b]pyridine;
and salts and prodrugs thereof.

Most aptly, the invention provides such a compound as its pharmaceutically acceptable salt.

The invention also provides pharmaceutical compositions comprising one or more of the novel compounds according to the invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. An erodible polymer containing the active agent may be envisaged. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Favoured unit dosage forms contain from 1 to 100 mg, for example 5, 10, 25 or 50 mg, of the active agent. The tablets or pills of the novel composition can be coated or otherwise compounded to provide a dosage form affording the advantage of prolonged action. For example, the tablet or pill can comprise an inner dosage and an outer dosage component, the letter being in the form of an envelope over the former. The two components can be separated by an enteric layer which serves to resist disintegration in the stomach and permits the inner component to pass intact into the duodenum or to be delayed in release. A variety of materials can be used for such enteric layers or coating, such materials including a number of polymer acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacenth, acacia, alginate, dextran, sodium carboxymethlcellulose, methylcellulose, polyvinylpyrrolidone or gelatin. These dosage forms may contain amounts of active agent as set forth hereinbefore in respect of solid unit dosage forms.

In the treatment of schizophrenia, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

In order to alleviate the symptoms of schizophrenia, including the positive and negative symptoms of schizophrenia, without causing sedation or extrapyramidal side-effects, the dosage level of the compound according to the invention is ideally selected such that the dose administered is effective in substantially completely blocking the dopamine $D_4$ receptor subtype in human brain whilst displaying no or negligible dopamine $D_2$ receptor subtype occupancy. A suitable dosage level in this regard is about 0.001 to 5.0 mg/kg per day, more particularly about 0.005 to 1.0 mg/kg per day, and especially about 0.01 to 0.5 mg/kg per day.

If desired, the methods of this invention may also comprise co-administration of another anti-schizophrenic medicament, for example one producing its effects via $D_2$ and/or $5-HT_2$ receptor blockade. In such circumstances, an enhanced anti-schizophrenic effect is envisaged without a corresponding increase in side-effects such as those caused by, for example, $D_2$ receptor subtype blockade; or a comparable anti-schizophrenic effect with reduced side-effects may alternatively be envisaged. Such co-administration may be desirable where a patient is already established on a conventional anti-schizophrenic medicament such as haloperidol, chlorpromazine or the like.

The compounds of formula I above, including the novel compounds according to the present invention, may be prepared by a process which comprises reacting a compound of formula III with a compound of formula IV:

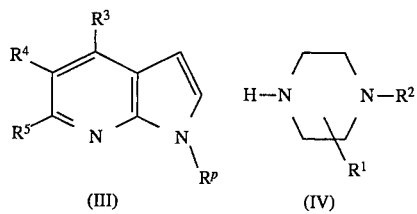

(III)            (IV)

wherein $R^1$, $R^2$, $R^3$, $R^4$ and $R^5$ are as defined above, and $R^P$ corresponds to the group R as defined above or represents a suitable protecting group; in the presence of a substantially equimolar amount of formaldehyde; followed, where required, by removal of the protecting group $R^P$; and subsequently, if necessary, N-alkylation by standard methods to introduce the moiety R.

The reaction is conveniently carried out by stirring the reactants in aqueous acetic acid, ideally in the presence of a buffer such as sodium acetate trihydrate, suitably at room temperature.

The formaldehyde may be utilised in the form of paraformaldehyde; or as a solution of formaldehyde in an inert solvent, e.g. 37% aqueous formaldehyde.

The protecting group $R^P$, when present, is suitably an acyl moiety such as acetyl, which can conveniently be removed as necessary by treatment under strongly basic conditions, e.g. sodium methoxide in methanol. Alternatively, the protecting group $R^P$ may be a carbamoyl moiety such as t-butoxycarbonyl (BOC), which can conveniently be removed as necessary by treatment under mildly acidic conditions.

In an alternative procedure, the compounds of formula I above, including the novel compounds according to the present invention, may be prepared by a process which comprises reacting a compound of formula IV as defined above with a compound of formula V:

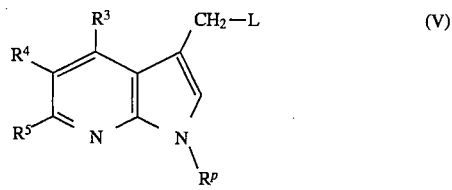

wherein $R^3$, $R^4$, $R^5$ and $R^P$ are as defined above, and L represents a suitable leaving group; followed, where required, by removal of the protecting group $R^P$; and subsequently, if necessary, N-alkylation by standard methods to introduce the moiety R.

The leaving group L is suitably a halogen atom, e.g. chlorine or bromide; or a dialkylamino group, e.g. dimethylamino.

When L represents a halogen atom, the reaction between compounds IV and V is conveniently carried out by stirring the reactants under basic conditions in a suitable solvent, for example potassium carbonate in N,N-dimethylformamide, or triethylamine in tetrahydrofuran or acetonitrile. Where L represents a dialkylamino group, the reaction is conveniently effected by heating the reactants in an inert solvent such as toluene, typically at the reflux temperature of the solvent.

Where they are not commercially available, the starting materials of formula III, IV and V may be prepared by procedures analogous to those described in the accompanying Examples, or by standard methods well known from the art.

It will be appreciated that any compound of formula I initially obtained from any of the above processes may, where appropriate, subsequently be elaborated into a further desired compound of formula I using techniques known from the art. For example, a compound of formula I wherein R is hydrogen initially obtained may be converted into a compound of formula I wherein R represents $C_{1-6}$ alkyl by standard alkylation techniques, such as by treatment with an alkyl iodide, e.g. methyl iodide, typically under basic conditions, e.g. sodium hydride in dimethylformamide, or triethylamine in acetonitrile. Moreover, a compound of formula I wherein the $R^2$ moiety is substituted by carboxy may be obtained from the corresponding alkyl ester derivative initially obtained by conventional deesterification procedures, typically by treatment with a base such as sodium hydroxide in a lower alkanol such as ethanol. Similarly, a compound of formula I wherein the $R^2$ moiety is substituted by an alkyl ester or carboxamide moiety initially obtained may be converted into the corresponding hydroxymethyl or aminomethyl derivative respectively by reduction with an appropriate reducing agent, e.g. diisobutylaluminium hydride or lithium aluminium hydride.

Where the above-described processes for the preparation of the compounds of use in the invention give rise to mixtures of stereoisomers, there isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-1-tartaric acid, followed by fractional crystallization and regeneration of the free base. The compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. the protecting groups may be removed at a convenient subsequent stage using methods known from the art.

The following Examples illustrate the preparation of compounds according to the invention.

The compounds useful in this invention potently inhibit [$^3$H]-spiperone binding to human dopamine $D_4$ receptor subtypes expressed in clonal cell lines. Moreover, the compounds useful in the invention display a selective affinity for the $D_4$ subtype relative to the $D_2$ subtype.

[$^3$H]-Spiperone Binding Studies

Clonal cell lines expressing the human dopamine $D_2$ and $D_4$ receptor subtype were harvested in PBS and then lysed in 10 mM Tris-HCl pH 7.4 buffer containing 5 mM MgSO$_4$ for 20 min on ice. Membranes were centrifuged at 50,000 g for 15 min at 4° C. and the resulting pellets resuspended in assay buffer (50 mM Tris-HCl pH 7.4 containing 5 mM EDTA, 1.5 mM CaCl$_2$, 5 mM MgCl$_2$, 5 mM KCl, 120 mM NaCl, and 0.1% ascorbic acid) at 20 mg/ml wet weight. Incubations were carried out for 60 min at room temperature (22° C.) in the presence of 0.05–2 nM [$^3$H]-spiperone or 0.2 nM for displacement studies and were initiated by addition of 20–100 µg protein in a final assay volume of 0.5 ml. The incubation was terminated by rapid filtration over GF/B filters presoaked in 0.3% PEI and washed with 10 ml ice-cold 50 mM Tris-HCl, pH 7.4. Specific binding was determined by 10 µM apomorphine and radioactivity determined by counting in a LKB beta counter. Binding parameters were determined by non-linear least squares regression analysis, from which the inhibition constant $K_i$ could be calculated for each test compound.

The compounds of the accompanying Examples were tested in the above assay, and all were found to possess a $K_i$ value for displacement of [$^3$H]-spiperone from the human dopamine $D_4$ receptor subtype of below 1.5 µM, for example 150 nM or less. Moreover, the compounds of the accompanying Examples are much more weakly active at the human dopamine $D_2$ receptor subtype.

By way of illustration, the compound of accompanying Example 2 has a $K_i$ value for the $D_4$ subtype of 1.3 nM and a $K_i$ value for the $D_2$ subtype in excess of 1500 nM, giving a $D_4$:$D_2$ ratio of greater than 1150. Similarly, the compound of accompanying Example 5 has $K_i$ values for the $D_4$ and $D_2$ subtypes of 0.43 nM and 860 nM respectively, giving a $D_4$:$D_2$ ratio of 2000.

By contrast, the compound of Example 9 of U.S. Pat. No. 3,362,956 (corresponding to Example 8 of U.S. Pat. No. 3,511,841) has been made and tested, and has been found to possess $K_i$ values for the $D_4$ and $D_2$ subtypes of 26 nM and 900 nM respectively, giving a $D_4$:$D_2$ ratio of only 35.

Side-effect Potential

1. Sedation

Representative compounds according to the invention have been tested for their effects on spontaneous motor activity occasioned by placing rats in novel cages equipped with photocells in order to determine the number of cage crossings. This is an art-recognised model of the sedation potential of a given test compound. By way of illustration, the compound of accompanying Example 5 was tested in this model and gave no evidence for sedation at doses of up to 10–30 mg/kg. On the other hand, with haloperidol, a classical neuroleptic agent acting at dopamine receptors in the striatum, marked sedation was observed at a dose of 1 mg/kg.

2. Extrapyramidal Disorders

Representative compounds according to the invention have been tested for their effect on apomorphine-induced stereotypy in the rat. This is an art-recognised model of the potential to induce extrapyramidal side-effects.

By way of illustration, the compound of accompanying Example 5 was tested in this model and displayed no potential to induce the extrapyramidal side-effects associated with dopamine receptors in the striatum at doses up to 1.0 mg/kg. By contrast, haloperidol, a classical neuroleptic agent acting at dopamine receptors in the striatum (vide supra), displayed a significant potential to elicit extrapyramidal side-effects at doses of 0.5 and 1.0 mg/kg.

EXAMPLE 1

3-(4-Phenylpiperazin-1-yl)methyl-1H-pyrrolo[2,3-b]pyridine

1-Phenylpiperazine (1.63 g, 10.0 mmol), and sodium acetate trihydrate (1.36 g, 10 mmol) were dissolved in acetic acid (4 ml) and water (2 ml). 37% Aqueous formaldehyde (0.9 ml, 12 mmol) was added and the reaction mixture stirred for five minutes. 1H-Pyrrolo[2,3-b]pyridine (1.18 g, 10 mmol) was added, and the resulting solution stirred at room temperature overnight. The reaction mixture was poured into 2M sodium hydroxide solution (50 ml) and extracted with ethyl acetate (2×50 ml). The extracts were washed with brine (50 ml), combined and dried (MgSO$_4$). The ethyl acetate solution was concentrated in vacuo to about one quarter of the original volume and the precipitated yellow solid was collected by filtration and recrystallised from toluene to yield the title compound (1.20 g), as pale lemon crystals. This material was further recrystallised from methanol to give pale lemon needles, m.p. 207°–209° C.; (Found: C, 73.91; H, 7.09; N, 19.31. C$_{18}$H$_{20}$N$_4$ requires C, 73.94; H, 6.90; N, 19.16%); $\delta_H$ (DMSO-d$_6$) 2.53 (4H, t, J 5 Hz, 2×C$\underline{H}_2$N), 3.10 (4H, t, J 5 Hz, 2×C$\underline{H}_2$N), 8.68 (2H, s, indole-C$\underline{H}_2$N), 6.75 (1H, t, J 7 Hz, 4'-H), 6.89 (2H, d, J 8 Hz, 2'-H, 6'-H), 7.04 (1H, dd, J 8, 4.5 Hz, 5-H), 7.18 (2H, t, J 8 Hz, 3'-H, 5'-H), 8.05 (1H, dd, J 8, 1.5 Hz, 4-H), 8.19 (1H, dd, J 4.5, 1.5 Hz, 6-H), and 11.45 (1H, br s, NH); m/z Cl$^+$, NH$_3$) 293 (M+1)$^+$.

Prepared in an analogous manner were:

EXAMPLE 2

3-(4-[4-Methoxyphenyl]piperazin-1-yl)methyl-1H-pyrrolo[2,3-b]pyridine

M.p. 213°–214° C. (PhMe); Found: C, 70.84; H, 6.75; N, 17.14. C$_{19}$H$_{22}$N$_4$O requires C, 70.78; H, 6.88; N, 17.38%); $\delta_H$ (DMSO-d$_6$) 2.49–2.53 (4H, m, 2×piperazinyl CH$_2$), 2.98 (4H, m, 2×piperazinyl CH$_2$), 3.66–3.67 (5H, m, C$\underline{H}_2$+OC$\underline{H}_3$), 6.77–6.86 (4H, m, ArH), 7.04 (1H, dd, J 7.9, 4.6 Hz, 5-H), 7.37 (1H, d, J 1.6 Hz, ArH), 8.04 (1H, dd, J 7.9, 1.5

Hz, 4-H), 8.19 (1H, dd, J 4.6, 1.5 Hz, 6-H), and 11.46 (1H, br s, NH); m/z (CI$^+$, NH$_3$) 323 (M+1)$^+$.

EXAMPLE 3

3-(4-Benzylpiperazin-1-yl)methyl-1H-pyrrolo[2,3-b]pyridine

M.p. 153° C. (MeOH); (Found: C, 74.35; H, 7.03; N, 18.17. C$_{19}$H$_{22}$N$_4$ requires C, 74.48; H, 7.24; N, 18.29%); δ$_H$ (DMSO-d$_6$) 2.36 (8H, br s, 4×CH$_2$), 3.42 (2H, s, CH$_2$), 3.60 (2H, s, CH$_2$), 7.01 (1H, dd, J 7.8, 4.6 Hz, 5-H), 7.19–7.31 (6H, m, ArH), 8.01 (1H, dd, J 7.8, 1.5 Hz, 4-H), 8.17 (1H, dd, J 4.6, 1.5 Hz, 6-H), and 11.41 (1H, br s, NH); m/z (CI$^+$, NH$_3$) 307 (M+1).

EXAMPLE 4

3-(4-[4-Ethylphenyl]piperazin-1-yl)methyl-1H-pyrrolo[2,3-b]pyridine

M.p. 216°–217° C. (MeOH); Found: C, 75.32; H, 7.36; N, 17.59. C$_{20}$H$_{24}$N$_4$ requires C, 74.97; H, 7.55; N, 17.48%); δ$_H$ (DMSO-d$_6$) 1.12 (3H, t, J 7.6 Hz, ArCH$_2$CH$_3$), 2.50 (6H, m, ArCH$_2$CH$_3$ and 2×piperazinyl CH$_2$), 3.05 (4H, m, 2×piperazinyl CH$_2$), 3.67 (2H, s, N—CH$_2$Ar), 6.81 (2H, d, J 8.6 Hz, ArH), 7.03 (3H, m, ArH), 7.37 (1H, d, J 2.2 Hz, 2-H), 8.05 (1H, dd, J 7.8, 1.4 Hz, 4-H), 8.19 (1H, dd, J 4.6, 1.4 Hz, 6-H), and 11.47 (1H, br s, NH); m/z (CI$^+$, NH$_3$) 321 (M+1)$^+$.

EXAMPLE 5

3-(4-[4-Chlorophenyl]piperazin-1-yl)methyl-1H-pyrrolo[2,3-b]pyridine

M.p. 226°–227° C. (MeOH); Found; C, 65.77; H, 5.78; N, 17.26. C$_{18}$H$_{19}$N$_4$Cl requires C, 66.15; H, 5.86; N, 17.14%); δ$_H$ (DMSO-d$_6$) 2.53 (4H, m 2×piperazinyl CH$_2$), 3.10 (4H, m, 2×piperazinyl CH$_2$), 3.67 (2H, s, CH$_2$—N), 6.90 (2H, d, J 9.0 Hz, ArH), 7.03 (1H, dd, J 7.8, 4.6 Hz, 5-H), 7.19 (2H, d, J 9.0 Hz, ArH), 7.37 (1H, d, J 2.4 Hz, 2-H), 8.04 (1H, dd, J 7.8, 1.6 Hz, 4-H), 8.19 (1H, dd, J 4.6, 1.6 Hz, 6-H), and 11.47 (1H, br s, NH); m/z (CI$^+$, NH$_3$) 327 (M+1)$^+$. The hydrochloride salt was prepared.

EXAMPLE 6

3-(4-[4-Ethoxyphenyl]piperazin-1-yl)methyl-1H-pyrrolo[2,3-b]pyridine

Step 1: 1-(tert-Butoxycarbonyl)-4-(4-hydroxyphenyl)piperazine

Di-tert-butyl dicarbonate (3.13 g, 14.3 mmol) was added to a suspension of 1-(4-hydroxyphenyl)piperazine (2.40 g, 13.5 mmol) in dichloromethane (60 ml) and the mixture stirred overnight at room temperature. The reaction mixture was filtered and the filtrate evaporated. Trituration with diethyl ether gave 1-(tert-Butoxycarbonyl)- 4-(4-hydroxyphenyl)piperazine as a buff solid (2.76 g, 74%); δ$_H$(CDCl$_3$) 1.48 (9H, s, C(CH$_3$)$_3$), 2.99 (4H, m, 2×piperazinyl CH$_2$), 3.58 (4H, m, 2×piperazinyl CH$_2$), 5.18 (1H, br s, ArOH), 6.77 (2H, m, ArH), and 6.85 (2H, m, ArH).

Step 2: 1-(4-Ethoxyphenyl)piperazine

Bromoethane (0.48 ml, 6.43 mmol) was added to a mixture of 1-(tert-butoxycarbonyl)-4-(4-hydroxyphenyl)piperazine (1.64 g, 5.89 mmol) and potassium carbonate (0.90 g, 6.51 mmol) in dimethylformamide (15 ml). The reaction mixture was stirred overnight and then more potassium carbonate (1.63 g, 11.8 mmol) and bromoethane (0.48 ml, 6.43 mmol) was added. The mixture was stirred at room temperature overnight, poured into water (150 ml) and extracted with ethyl acetate (2×100 ml). The extracts were washed with brine (100 ml), combined, and dried (MgSO$_4$). Evaporation of the solvent gave a buff solid (1.71 g). This was dissolved in dichloromethane (20 ml), trifluoroacetic acid (10 ml) added and the reaction mixture stirred at room temperature under nitrogen for 30 minutes. The mixture was concentrated in vacuo, the residue dissolved in 1M hydrochloric acid (50 ml) and washed with dichloromethane (2×25 ml). The aqueous phase was basified with 4M sodium hydroxide (30 ml) and extracted with ethyl acetate (2×50 ml). The extracts were washed with brine (50 ml), combined, dried (MgSO$_4$) and concentrated in vacuo to give 1-(4-ethoxyphenyl) piperazine (1.03 g, 89%) as a beige solid; δ$_H$ (CDCl$_3$) 1.38 (3H, t, J 7.0 Hz, ArCH$_2$CH$_3$), 1.84 (1H, br s, NH), 3.04 (8H, s, 4×piperazinyl CH$_2$), 3.98 (2H, q, J 7.0 Hz, ArCH$_2$CH$_3$), and 6.82–6.91 (4H, m, ArH).

Step 3: 3-(4-[4-Ethoxyphenyl]piperazin-1-yl)methyl-1H-pyrrolo[2,3-b]pyridine

A mixture of 3-dimethylaminomethyl-1H-pyrrolo[2,3-b]pyridine [prepared by the method of M. M. Robinson and B. L. Robinson, *J. Am. Chem. Soc.*, 1955, 77, 457] (0.40 g, 2.28 mmol) and 1-(4-ethoxyphenyl)piperazine (0.495 g, 2.40 mmol) in toluene (10 ml) was heated at reflux under nitrogen for 7 h. The mixture was allowed to cool and the crystallised product collected. Recrystallisation from methanol afforded the title compound (0.513 g, 67%), m.p. 179°–180° C.; (Found: C, 71.27; H, 7.19; N, 16.59. C$_{20}$H$_{24}$N$_4$O requires C, 71.40; H, 7.19; N, 16.65%); δ$_H$ (DMSO-d$_6$) 1.27 (3H, t, J 7.0 Hz, ArOCH$_2$CH$_3$), 2.52 (4H, m, 2×piperazinyl CH$_2$), 2.98 (4H, m, 2×piperazinyl CH$_2$), 3.67 (2H, s, CH$_2$N), 3.92 (2H, q, J 7.0 Hz, ArOCH$_2$CH$_3$), 6.80 (4H, m, ArH), 7.04 (1H, dd, J 7.8, 4.6 Hz, 5-H), 7.37 (1H, d, J 2.1 Hz, 2-H), 8.04 (1H, dd, J 7.8, 1.3 Hz, 4-H), 8.19 (1H, dd, J 4.6, 1.3 Hz, 6-H), and 11.46 (1H, br s, NH); m/z (CI$^+$, NH$_3$) 337 (M+1)$^+$.

EXAMPLE 7

3-(4-[4-Dimethylaminophenyl]piperazin-1-yl)methyl-1H-pyrrolo[2,3-b]pyridine

Step 1: 1-(tert-Butoxycarbonyl)-4-(4-dimethylaminophenyl)piperazine

Di-tert-butyl dicarbonate (3.11 g, 14.2 mmol) was added to a solution of 1-(4-nitrophenyl)piperazine (2.96 g, 14.3 mmol) in dichloromethane (100 ml). The resulting solution was stirred for 3 h at room temperature and then concentrated in vacuo to a yellow solid (4.37 g). The solid was dissolved in ethanol (200 ml), a 37% aqueous solution of formaldehyde (3.2 ml, 43 mmol) and 10% palladium on carbon (0.40 g) were added and the mixture hydrogenated on a Parr apparatus (maximum 50 psi) for 8 h. Further portions of aqueous formaldehyde (1.0 ml) and 10% palladium on carbon (0.10 g) were added and the reaction mixture hydrogenated overnight. This procedure was repeated to ensure complete formation of the desired product. The reaction mixture was filtered and the filtrate concentrated to an oil which was treated with silica gel in ethyl acetate. The mixture was filtered and concentrated to give 1-tert-butoxycarbonyl)-4-(4-dimethylaminophenyl)piperazine (4.25 g, 98%) as an off-white crystalline solid: δ$_H$ (DMSO-d$_6$) 1.41 (9H, s, C(CH$_3$)$_3$), 2.78 (6H, s, N(CH$_3$)$_2$), 2.89 (4H, m, 2×piperazinyl CH$_3$), 3.44 (4H, m, 2×piperazinyl (CH$_2$), 6.68 (2H, m, ArH), and 6.84 (2H, m, ArH).

Step 2: 1-(4-Dimethylaminophenyl)piperazine

Trifluoroacetic acid (10 ml) was added to a solution of 1-tert-butoxycarbonyl)-4-(4-dimethylaminophenyl)piperazine (2.01 g 6.58 mmol) in dichloromethane (20 ml) and the mixture stirred for 30 min at room temperature. The mixture was concentrated in vacuo and saturated aqueous potassium carbonate (100 ml) was cautiously added to the residue. The mixture was extracted with dichloromethane (3×100 ml), the extracts were washed with brine (50 ml), combined and dried (MgSO$_4$). Concentration of the extracts gave 1-(4-dimethylaminophenyl)piperazine (1.14 g, 84% as a cream solid; $\delta_H$ (DMSO-d$_6$) 2.77 (6H, s, N(CH$_3$)$_2$), 2.79 (4H, m, 2×piperazinyl CH$_2$), 2.86 (4H, m, 2×piperazinyl CH$_2$), 6.68 (2H, m, ArH), and 6.82 (2H, m, ArH).

Step 3: 3-(4-[4-Dimethylaminophenyl]piperazin-1-yl)methyl-1H-pyrrolo[2,3-b]pyridine A mixture of 3-dimethylaminomethyl-1H-pyrrolo[2,3-b]pyridine (0.4450 g, 2.54 mmol) and 1-(4-dimethylaminophenyl)piperazine (0.55 g, 2.68 mmol) in toluene (20 ml) was heated at reflux under nitrogen for 7 h. The mixture was allowed to cool and the solid formed was collected. Recrystallisation from methanol gave the title compound (0.382 g, 45%) as colourless needles, m.p. 199°–201° C.; (Found: C, 71.32; H, 7.37; N, 20.71. C$_{20}$H$_{25}$N$_5$ requires C, 71.61; H, 7.51; N, 20.88%); $\delta_H$ (DMSO-d$_6$) 2.52 (4H, m, 2×piperazinyl CH$_2$), 2.76 (6H, s, N(CH$_3$)$_2$), 2.95 (4H, m, 2×piperazinyl CH$_2$), 3.67 (2H, s, CH$_2$N), 6.66 (2H, m, ArH), 6.80 (2H, m, ArH), 7.03 (1H, dd, J 7.8, 4.7 Hz), 7.35 (1H, d, J 2.0 Hz, 2-H), 8.04 (1H, dd, J 7.8, 1.5 Hz, 4-H), 8.19 (1H, dd, J 4.7, 1.5 Hz, 6-H), and 11.41 (1H, br s, NH); m/z (CI$^+$, NH$_3$) 336 (M+1)$^+$.

EXAMPLE 8

3-(4-[3,4-Dichlorophenyl]piperazin-1-yl)methyl-1H-pyrrolo[2,3-b]pyridine

M.p. 219°–220° C. (MeOH); Found: C, 60.05; H, 5.18; N, 15.32. C$_{18}$H$_{18}$Cl$_2$N$_4$ requires C, 59.84; H, 5.02; N, 15.51%); $\delta_H$ (DMSO-d$_6$) 2.50 (4H, m, 2×piperazinyl CH$_2$), 3.15 (4H, m, 2×piperazinyl CH$_2$), 8.67 (2H, s, CH$_2$N), 6.89 (1H, dd, J 2.9, 9.0 Hz, 6'-H), 7.04 (1H, dd, J 7.8, 4.7 Hz, 5-H), 7.09 (1H, d, J 2.9 Hz, 2'-H), 7.36 (2H, m, 2-H, 5'-H), 8.05 (1H, dd, J 7.8, 1.5 Hz, 4-H), 8.20 (1H, dd, J 4.7, 1.5 Hz, 6-H), 11.48 (1H, br s, NH); m/z (CI$^+$, NH$_2$) 361 [(M+1)$^+$, $^{35}$Cl$_2$].

EXAMPLE 9

3-(4-[4-Methoxyphenyl]piperazin-1-yl)methyl-1-methyl-1H-pyrrolo[2,3-b]pyridine

Sodium hydride (80% dispersion in oil; 0.13 g, 4.3 mmol) was added to a solution of 3-(4-(4-methoxyphenyl)piperazin-1-yl)methyl-1H-pyrrolo[2,3-b]pyridine (1.06 g, 3.29 mmol) in dimethylformamide (30 ml) at 0° C. The cooling bath was removed and the mixture stirred at room temperature for an hour. Methyl iodide (0.22 ml, 3.53 mmol) was added and the reaction mixture stirred for 2 h at room temperature. The mixture was poured into water (300 ml), extracted with ethyl acetate (2×150 ml), and the extracts washed with brine (150 ml). The combined extracts were dried (MgSO$_4$) and evaporated to give a yellow solid. Purification by flash chromatography, eluting with 5% then 7.5% methanol in dichloromethane, gave the title compound (0.87 g, 79%). Recrstallisation from ethyl acetate/petrol (60°–80° C.) gave fine needles, m.p. 92°–94° C.; (Found: C, 71.25; H, 7.18; N, 16.49. C$_{20}$H$_{24}$N$_4$O requires C, 71.40; H, 7.19; N, 16.65%); $\delta_H$ (CDCl$_3$) 2.65 (4H, m, 2×piperazinyl CH$_2$), 3.09 (4H, m, 2×piperazinyl CH$_2$), 3.74 (2H, s, CH$_2$N), 3.75 (3H, s, ArOCH$_3$), 3.87 (3H, s, N—CH$_3$), 6.85 (4H, m, ArH), 7.05 (1H, dd, J 7.8, 4.7 Hz, 5-H), 7.15 (1H, br s, 2H), 8.04 (1H, dd, J 7.8, 1.5 Hz, 4-H), and 8.33 (1H, dd, J 4.7, 1.5 Hz, 6-H); m/z (CI$^+$, NH$_3$) 337 (M+1)$^+$.

EXAMPLE 10

3-(4-[5-Chloro-2-pyridiyl]piperazin-1-yl)methyl-1H-pyrrolo[2,3-b]pyridine

A mixture of 2,5-dichloropyridine (10.0 g, 67.6 mmol) and piperazine (58.1 g, 675 mmol) was stirred at 165° C. for 2 H. The mixture was allowed to cool, slurried with dichloromethane (200 ml) and the solid collected by filtration. The filtrate was concentrated in vacuo and the procedure repeated. The residue after concentration of the filtrate was purified by flash chromatography twice (eluting with 1% ammonia, 10% methanol in dichloromethane) to give 1-(5-chloro-2-pyridyl)piperazine (12.25 g, 92%) as a tan solid. A portion of this solid (0.484 g, 2.45 mmol) was added to a solution of 3-dimethylaminomethyl-1H-pyrrolo[2,3-b]pyridine (0.392 g, 2.24 mmol) in toluene (10 ml) and the mixture heated at reflux under nitrogen for 6 h. The mixture was allowed to cool and the crystallised product filtered off. Recrystallisation from toluene gave the title compound (0.229 g, 31%), m.p. 196°–198° C.; (Found: C, 63.16; H, 5.60; N, 21.18. C$_{17}$H$_{18}$ClN$_5$. 0.1PhMe requires C, 63.08; H, 5.62; N, 20.78%); $\delta_H$ (DMSO-d$_6$) 2.46 (4H, t, J 5.0 Hz, 2×piperazinyl CH$_2$), 3.45 (4H, t, J 5.0 Hz, 2×piperazinyl CH$_2$), 3.67 (2H, s, CH$_2$N), 6.82 (1H, d, J 9.1 Hz, 3'-H), 7.04 (1H, dd, J 7.8, 4.6 Hz, 5-H), 7.37 (1H, d, J 2.1 Hz, 2-H), 7.56 (1H, dd, J 9.1, 2.7 Hz, 4'-H), 8.05 (1H, dd, J 7.8, 1.4 Hz, 4-H), 8.08 (1H, d, J 2.7 Hz, 6'-H), 8.19 (1H, dd, J 4.6, 1.4 Hz, 6-H), and 11.46 (1H, br s, NH); m/z (CI$^+$, NH$_3$) 328 [(M+H)$^+$, $^{\pm}$Cl].

EXAMPLE 11

3-(4-[3-Isoquinolyl]piperazin-1-yl)methyl-1H-pyrrolo[2,3-b]pyridine

Prepared by the method outlined in the previous example from the trifluoromethanesulphonate derived from 3-hydroxyisoquinoline.

M.p. 246°–248° C. (dec.) (EtOH); (Found: C, 72.15; H, 6.11; N, 19.92. C$_{21}$H$_{21}$N$_5$.0.35H$_2$O requires C, 72.12; H, 6.25; N, 20.02%), $\delta_H$ (DMSO-d$_6$) 2.55 (4H, m, 2×piperazinyl CH$_2$), 3.51 (4H, m, 2×piperazinyl CH$_2$), 3.70 (2H, s, CH$_2$N), 6.94 (1H, s, 4'-H), 7.05 (1H, dd, J 7.8, 4.7 Hz, 5-H), 7.28 (1H, m, 6'-H or 7'-H), 7.39 (1H, s, 2-H), 7.52 (1H, m, 7'-H or 6'H), 7.64 (1H, m, 5'-H or 8'-H), 7.85 (1H, m, 8'-H or 5'-H), 8.08 (1H, dd, J 7.8, 1.5 Hz, 4-H), 8.20 (1H, dd, J 4.7, 1.5 Hz, 6-H), and 11.48 (1H, br s, NH); m/z (CI$^+$, NH$_3$) 344 (M+1)$^+$.

EXAMPLE 12

3-(4-[5-Indolyl]piperazin-1-yl)methyl-1H-pyrrolo[2,3-b]pyridine
Step 1: 1-(5-Indolyl)piperazine Bis(2-chloroethyl)amine hydrochloride (3.60 g, 20.2 mmol) was added to a suspension of 5-aminoindole (2.53 g, 19.1 mmol) in ethanol (30 ml) and the mixture heated at reflux for 16 h. The mixture was allowed to cool, sodium carbonate (2.14 g, 20.2 mmol) was added and the reaction mixture heated at reflux for 8 h. The mixture was allowed to cool, filtered and the filtrate evaporated. The residue was dissolved in 1M hydrochloric acid (100 ml) and extracted with dichloromethane (2×50 ml). The aqueous phase was made basic with 4M sodium hydroxide (30 ml) and extracted with ethyl acetate (2×100 ml). The extracts were washed with brine (100 ml), combined and dried (MgSO$_4$). The residue from evaporation of the extracts was purified by flash chromatography, eluting with dichloromethane/methanol/ammonia, to give 1-(5-indolyl)piperazine (0.71 g, 18%), as a cream solid; $\delta_H$ (DMSO-d$_6$) 2.94 (4H, m, 2×piperazinyl CH$_2$), 3.00 (4H, m, 2×piperazinyl CH$_2$), 6.29 (1H, m, 3-H), 6.84 (1H, dd, J 9.0, 2.0 Hz, 6-H), 7.00 (1H, d, J 2.0 Hz, 2-H), 7.24 (2H, m, 4-H), and 10.82 (1H, br s, NH).

Step 2: 3-(4-[5-Indolyl]piperazin-1-yl)methyl-1H-pyrrolo[2,3-b]pyridine

A mixture of 3-dimethylaminomethyl-1H-pyrrolo[2,3-b]pyridine (0.23 g, 1.33 mmol) and 1-(5-indolyl)piperazine (0.27 g, 1.34 mmol) in toluene (20 ml) was heated at reflux for 16 h under nitrogen. The mixture was allowed to cool and the solid present collected. Purification by flash chromatography, eluting with 90:8:1 dichloromethane/methanol/ammonia, twice gave the title compound (0.14 g, 32%) as a white solid. Recrystallisation from methanol afforded needles, m.p. 232.5°–233° C.; (Found: C, 72.14; H, 6.29; N, 21.07. $C_{20}H_{21}N_5 \cdot 0.1H_2O$ requires C, 72.09; H, 6.41; N, 21.02%); $\delta_H$ (DMSO-$d_6$) 2.56 (4H, m, 2×piperazinyl $CH_2$), 3.02 (4H, m, 2×piperazinyl $CH_2$), 3.69 (1H, s, $CH_2N$), 6.27 (1H, m, 3'-H), 6.83 (1H, dd, J 8.8, 2.1 Hz, 6'-H), 6.97 (1H, m, 2'-H), 7.05 (1H, dd, J 7.8, 4.6 Hz, 5-H), 7.22 (2H, m, 4'-H, 7'-H), 7.38 (1H, d, J 2.1 Hz, 2-H), 8.06 (1H, dd, J 7.8, 1.4 Hz, 4-H), 8.20 (1H, dd, J 4.6, 1.4 Hz, 6-H), 10.77 (1H, br s, NH), and 11.46 (1H, br s NH); m/z (CI$^+$, NH$_3$) 322 (M+1)$^+$.

EXAMPLE 13

3-(4-[4-Iodophenyl]piperazin-1-yl)methyl-1H-pyrrolo[2,3-b]pyridine

M.p. 223°–225° C. (dec.) (MeOH); (Found: C, 51.85; H, 4.50; N, 13.12. $C_{18}H_{19}N_4I$ requires C, 51.69; H, 4.58; N, 13.39%); $\delta_H$ (DMSO-$d_6$) 2.50 (4H, m, 2×piperazinyl $CH_2$), 3.10 (4H, m, 2×piperazinyl $CH_2$), 3.67 (2H, s, $CH_2N$), 6.74 (2H, d, J 9.0 Hz, ArH), 7.04 (1H, dd, J 7.8, 4.7 Hz, 5-H), 7.37 (1H, d, J 2.0 Hz, 2-H), 7.46 (2H, d, J 9.0 Hz, ArH), 8.05 (1H, dd, J 7.8, 1.4 Hz, 4-H), 8.19 (1H, dd, J 4.7, 1.4 Hz, 6-H), and 11.47 (1H, br s, NH); m/z (CI$^+$, NH$_3$) 419 (M+1)$^+$.

EXAMPLE 14

3-(4-[4-(Trifluoromethyl)phenyl]piperazin-1-yl)methyl-1H-pyrrolo[2,3-b]pyridine

M.p. 247°–250° C. (dec.) (MeOH); Found: C, 63.44; H, 5.29; N, 15.38. $C_{19}H_{19}F_3N_4$ requires C, 63.32; H, 5.31; N, 15.55%), $\delta_H$ (DMSO-$d_6$) 2.51 (4H, m, 2×piperazinyl $CH_2$), 3.26 (4H, m, 2×piperazinyl $CH_2$), 3.68 (2H, s, $CH_2N$), 7.04 (3H, m, 5-H+2×ArH), 7.38 (1H, br s, 2-H), 7.48 (2H, d, J 8.6 Hz, ArH), 8.05 (1H, br d, J 8 Hz, 4-H), 8.20 (1H, m, 6-H), and 11.47 (1H, br s, NH); m/z CI$^+$, NH$_3$) 361 (M+1)$^+$.

EXAMPLE 15

3-(4-[2-Phenoxyethyl]piperazin-1-yl)methyl-1H-pyrrolo[2,3-b]pyridine

M.p. 143° C. (EtOAc); (Found: C, 71.39; H, 7.19; N, 16.35. $C_{20}H_{24}N_4O$ requires C, 71.40; H, 7.19; H, 16.65%), $\delta_H$ (DMSO-$d_6$) 2.40 (4H, br s, 2×$CH_2$), 2.47 (4H, br s, 2×$CH_2$) 2.66 (2H, t, J 5.8 Hz, N$CH_2$CH$_2$O), 3.60 (2H, s, $CH_2$), 4.03 (2H, t, J 5.8 Hz, NCH$_2$$CH_2$O), 6.89 (3H, m, ArH), 7.03 (H, dd, J 7.8, 4.7 Hz, 5-H), 7.26 (2H, t, J 3.4 Hz, ArH), 7.32 (1H, d, 2.1 Hz, 2-H), 8.00 (H, dd, J 7.8, 1.2 Hz, 4-H), 8.18 (H, dd, J 4.7, 1.5 Hz, 6-H), and 11.42 (H, br s, NH); m/z (CI$^+$, NH$_3$) 337 (M+1).

EXAMPLE 16

3-(4-[4-Methylphenyl]piperazin-1-yl)methyl-1H-pyrrolo[2,3-b]pyridine

M.p. 220°–222° C. (MeOH); (Found: C, 74.24; H, 7.12; N, 18.32. $C_{19}H_{22}N_4$ requires: C, 74.48; H, 7.24; N, 18.29%); $\delta_H$ (DMSO-$d_6$) 2.18 (3H, s, ArCH$_3$), 2.04–2.53 (4H, m, 2×piperazinyl $CH_2$), 3.04 (4H, t, J 4.8 Hz, 2×piperazinyl $CH_2$), 3.67 (2H, s, NH$H_2$Ar), 5.79 (2H, d, 8.5 Hz, ArH), 6.99 (2H, d, J 8.5 Hz, ArH), 7.03 (1H, dd, J 7.8, 4.7 Hz, 5-H), 7.36 (1H, d, J 2.2 Hz, 2-H), 8.04 (1H, dd, J 7.8, 1.3 Hz, 4-H), 8.19 (1H, dd, J 4.7, 1.5 Hz, 6-H), and 11.45 (1H, br s, N—H); m/z (CI$^+$, NH$_3$) 307 (M+1)$^+$.

EXAMPLE 17

3-(4-[4-Fluorophenyl]piperazin-1-yl)methyl-1-H-pyrrolo[2,3-b]pyridine

M.p. 214°–216° C. (MeOH); (Found: C, 69.42; H, 6.29; N, 17.91. $C_{18}H_{19}N_4F$ requires C, 69.66; H, 6.17; N, 18.05%); $\delta_H$ (DMSO-$d_6$) 2.49–2.53 (4H, m, 2×piperazinyl $CH_2$), 3.04 (4h, t, J 4.8 Hz, 2×piperazinyl $CH_2$), 3.68 (2H, s, NCH$_2$Ar), 6.88–6.93 (2H, m, ArH), 6.98–705 (3H, m, ArH), 7.37 (1H, d, J 2.3 Hz, 2-H), 8.04 (1H, dd, J 7.8, 1.3 Hz, 4-H), 8.19 (1H, dd, J 4.7, 1.5 Hz, 6-H), and 11.47 (1H, br s, NH); m/z (CI$^+$, NH$_3$) 311 (M+1)$^+$.

EXAMPLE 18

3-(4-[1-Methyl-5-indolyl]piperazin-1-yl)methyl-1H-pyrrolo[2,3-b]pyridine

Step 1: 1-(tert-Butoxycarbonyl)-4-(1-methyl-5-indolyl)piperazine

Di-tert-butyldicarbonate (0.46 g, 2.11 mmol) was added to a solution of 1-(5-indolyl)piperazine (0.41 g, 2.04 mmol) in dimethylformamide/tetrahydrofuran (1:1, 20 ml) and the mixture stirred at room temperature overnight. The mixture was poured into water (200 ml) and extracted with ethyl acetate (2×100 ml). The extracts were washed with brine (100 ml), combined and dried (MgSO$_4$). The residue after evaporation of the solvent was dissolved in tetrahydrofuran (5 ml). Sodium hydride (80% dispersion in oil; 0.068 g, 2.27 mmol) was added and the mixture stirred at room temperature for thirty minutes. Methyl iodide (0.14 ml, 2.25 mmol) was added, the reaction mixture was stirred for 90 minutes then poured into water (50 ml) and extracted with ethyl acetate (2×50 ml). The extracts were washed with brine (50 ml), combined and dried (MgSO$_4$). Purification of the residue by flash chromatography, eluting with 1:3 then 1:2 ethyl acetate/petrol, gave the title compound (0.218 g, 34%) as a waxy solid; $\delta_H$ (CDCl$_3$) 1.49 (9H, s, C(CH$_3$)$_3$), 3.08 (4H, t, J 4.8 Hz, 2×piperazinyl $CH_2$), 3.62 (4H, t, J 4.8 Hz, 2×piperazinyl $CH_2$), 3.76 (3H, s, N—CH$_3$), 6.39 (1H, d, J 3.0 Hz, 3'-H), 7.00 (2H, m, 2-H, 5-H), and 7.24 (1H, d, J 9.1 Hz, 7-H).

Step 2: 3-(4-[1-Methyl-5-indolyl]piperazin-1-yl)methyl-1H-pyrrolo[2,3-b]pyridine Trifluoroacetic acid (5 ml) was added to a solution of 1-tert-butoxycarbonyl)-4-(1-methyl-5-indolyl)piperazine (0.2102 g, 0.666 mmol) in dichloromethane (5 ml) and the mixture stirred for 30 minutes at room temperature. The mixture was concentrated in vacuo and saturated aqueous potassium carbonate (20 ml) was added to the residue. The mixture was extracted with dichloromethane (2×20 ml), the extracts washed with brine (20 ml), combined and dried (MgSO$_4$). The extracts were concentrated and the residual yellow solid redissolved in toluene (5 ml). 3-Dimethylaminomethyl-1H-pyrrolo[2,3-b]pyridine (0.1136 g, 0.648 mmol) was added and the mixture heated at reflux under nitrogen for 5 hours. The mixture was allowed to cool and the solid present collected. Purification by flash chromatography, eluting with 120:8:1 then 90:8:1 dichloromethane/methanol/ammonia, gave the title compound (0.1433 g, 64%) as a yellow solid. Recrystallisation from methanol afforded pale yellow needles, m.p. 222°–223° C.; (Found: C, 72.81; H, 6.81; N, 20.17. $C_{21}H_{23}N_5$ requires C, 73.02; H, 6.71; N, 20.27%); $\delta_H$ (DMSO-$d_6$) 2.57 (4H, m, 2×piperazinyl CH$_2$), 3.03 (4H, m, 2×piperazinyl CH$_2$), 3.69 (2H, s, CH$_2$N), 3.71 (3H, s, N—CH$_3$), 6.25 (1H, d, J 2.9 Hz, 3'-H), 6.89 (1H, dd, J 8.9, 2.1 Hz, 6'-H), 6.98 (1H, d, J 2.0 Hz, 2-H or 4'-H), 6.98 (1H, d, J 2.9 Hz, 2'-H), 7.26 (1H, d, J 8.9 Hz, 7'-H), 7.38 (1H, d, J 2.1 Hz, 4'-H) or 2-H), 8.07 (1H, dd, J 7.8, 1.4 Hz, 4-H), 8.20 (1H, dd, J 4.6, 1.4 Hz, 6-H), and 11.46 (1H, br s, NH); m/z (CI$^+$, NH$_2$) 346 (M+1)$^+$.

EXAMPLE 19

3-(4-[5-Indazolyl]piperazin-1-yl)methyl-1H-pyrrolo[2,3-b]pyridine

Prepared in an analogous manner to 3-(4-[5-indolyl)piperazin-1-yl)methyl-1H-pyrrolo[2,3-b]pyridine (Example 12).

M.p. 238°–239.5° C. (dec.) (MeOH); Found; C, 68.39; H, 6.07; N, 25.34. C$_{19}$H$_{20}$N$_8$ requires C, 68.65; H, 6.06; N, 25.28%); δ$_H$ (DMSO-d$_6$) 2.57 (4H, m, 2×piperazinyl CH$_2$), 3.06 (4H, m, 2×piperazinyl CH$_2$), 3.70 (2H, s, CH$_2$N), 7.05 (2H, m, 5-H, 4'-H), 7.15 (1H, dd, J 9.1, 2.1 Hz, 6'-H), 7.38 (2H, m, 2-H, 7'-H), 7.87 (1H, s, 3'-H), 8.06 (1H, dd, J 7.8, 1.4 Hz, 4-H), 8.20 (1H, dd, J 4.7, 1.5 Hz, 6-H), 11.48 (1H, br s, NH), and 12.77 (1H, br s, NH); m/z (CI$^+$, NH$_2$) 333 (M+1)$^+$.

EXAMPLE 20

3-(4-[4-Ethoxycarbonylphenyl]piperazin-1-yl)methyl-1H-pyrrolo[2,3-b]pyridine

M.p. 196°–197° C. (EtOH); (Found: C, 69.04; H, 6.57; N, 15.20. C$_{21}$H$_{24}$N$_4$O$_2$ requires C, 69.21; H; 6.64; N, 15.37%); δ$_H$ (DMSO-d$_6$) 1.28 (3H, t, J 7.1 Hz, OCH$_2$CH$_3$), 2.50 (4H, m, 2×piperazinyl CH$_2$), 3.30 (4H, m, 2×piperazinyl CH$_2$), 3.69 (2H, s, CH$_2$N), 4.23 (2H, q, J 7.1 Hz, OCH$_2$CH$_3$), 6.94 (2H, d, J 9.0 Hz, ArH), 7.04 (1H, dd, J 7.8, 4.6 Hz, 5-H), 7.38 (1H, d, J 2.2 Hz, 2-H), 7.76 (2H, d, J 9.0 Hz, ArH), 8.05 (1H, dd, J 7.8, 1.4 Hz, 4-H), 8.20 (1H, dd, J 4.6, 1.4 Hz, 6-H), and 11.47 (1H, br s, NH); m/z (CI$^+$, NH$_3$) 365 (M+1)$^+$.

EXAMPLE 21

3-(4-[4-Carboxyphenyl]piperazin-1-yl)methyl-1H-pyrrolo[2,3-b]pyridine

A suspension of 3-(4-[4-ethoxycarbonylphenyl]piperazin-1yl)methyl-1H-pyrrolo-2,3-b]pyridine (0.6594 g, 1.81 mmol) in ethanol (50 ml) containing 1M aqueous sodium hydroxide (10.5 ml, 10.8 mmol) was stirred at room temperature for eight days, during which time the solid slowly dissolved. The reaction mixture was concentrated to a small volume, diluted with water and neutralised (pH 6–7) with acetic acid to give a gum which solidified on standing. The solid was collected, washed with water and dried in vacuo. Recrystallisation from dimethylformamide/water gave the title compound (0.4069 g, 67%) as a white solid, m.p. >250° C. (dec.); (Found: C, 66.96; H, 5.88; N, 16.30. C$_{19}$H$_{20}$N$_4$O$_2$.0.25H$_2$O requires C, 66.94; H, 6.06; N, 16.44); δ$_H$ (DMSO-d$_6$) 2.51 (4H, m, 2×piperazinyl CH$_2$), 3.27 (4H, m, 2×piperazinyl CH$_2$), 3.68 (2H, s, CH$_2$N), 6.93 (2H, d, J 9.0 Hz, ArH), 7.04 (1H, dd, J 7.8, 4.7 Hz, 5-H), 7.38 (1H, d, J 2.2 Hz, 2-H), 7.57 (2H, d, J 9.0 Hz, ArH), 8.06 (1H, dd, J 7.8, 1.4 Hz, 4-H), 8.20 (1H, dd, J 4.7, 1.4 Hz, 6-H), and 11.48 (1H, br s, NH); m/z (CI$^+$, NH$_3$) 337 (M+1)$^+$.

EXAMPLE 22

3-(4-[3-Methylphenyl]piperazin-1-yl)methyl-1H-pyrrolo[2,3-b]pyridine

M.p. 156°–158° C. (MeOH); (Found: C, 73.73; H, 7.12; N, 17.99. C$_{19}$H$_{22}$N$_4$.0.2H$_2$O requires C, 73.61; H, 7.28; N, 18.07%); δ$_H$ (DMSO-d$_6$) 2.22 (3H, s, ArCH$_3$), 2.51 (4H, m, 2×piperazinyl CH$_2$), 3.09 (4H, m, 2×piperazinyl CH$_2$), 3.67 (2H, s, CH$_2$N), 6.57 (1H, m, ArH), 6.70 (2H, m, ArH), 7.05 (2H, m, 5-H, ArH), 7.38 (1H, d, 2.3 Hz, 2-H), 8.05 (1H, m, 4-H), 8.19 (1H, dd, J 4.6, 1.5 Hz, 6-H), and 11.48 (1H, br s, NH); m/z (CI$^+$, NH$_3$) 307 (M+1)$^+$.

EXAMPLE 23

3-(4-[2-Methylphenyl]piperazin-1-yl)methyl-1H-pyrrolo[2,3-b]pyridine

M.p. 174°–176° C. (MeOH); (Found: C, 74.29; H, 7.18; N, 18.11. C$_{19}$N$_{22}$N$_4$ requires C, 74.48; H, 7.24; N, 18.29%); δ$_H$ (DMSO-d$_6$) 2.21 (3H, s, ArCH$_3$), 2.55 (4H, br s, 2×piperazinyl CH$_2$), 2.81 (4H, m, 2×piperazinyl CH$_2$), 3.70 (2H, s, CH$_2$N), 6.92 (1H, m, ArH), 6.99 (1H, m, ArH), 7.04 (1H, dd, J 7.8, 4.7 Hz, 5-H), 7.09 (2H, m, ArH), 7.37 (1H, d, J 2.2 Hz, 2-H), 8.06 (1H, dd, J 7.8, 1.3 Hz, 4-H), 8.20 (1H, dd, J 4.7, 1.5 Hz, 6-H), and 11.46 (1H, br s, NH); m/z (CI$^+$, NH$_3$) 307 (M+1)$^+$.

EXAMPLE 24

3-(4-[3,4-Methylenedioxyphenyl]piperazin-1-yl)methyl-1H-pyrrolo[2,3-b]pyridine

M.p. 196°–199° C. (PhMe); (Found: C, 67.69; H, 6.03; N, 16.48. C$_{19}$H$_{20}$N$_4$O$_2$ requires C, 67.84; H, 5.99; N, 16.66%); δ$_H$ (DMSO-d$_6$) 2.50 (4H, m, 2×piperazinyl CH$_2$), 2.98 (4H, m, 2×piperazinyl CH$_2$), 3.67 (2H, s, CH$_2$N), 5.89 (2H, s, OCH$_2$O), 6.30 (1H, dd, J 8.5, 2.3 Hz, 6'-H), 6.62 (1H, d, J 2.3 Hz, 2'-H), 6.73 (1H, d J 8.5 Hz, 5'-H), 7.04 (1H, dd, 7.8, 4.6 Hz, 5-H), 7.36 (1H, br s, 2-H), 8.04 (1H, m, 4-H), 8.19 (1H, m, 6-H), and 11.43 (1H, br s, NH); m/z (CI$^+$, NH$_3$) 337 (M+1)$^+$.

EXAMPLE 25

(3-(4-[4-Bromophenyl]piperazin-1-yl)methyl-1H-pyrrolo[2,3-b]pyridine

M.p. 234°–238° C. (MeOH); (Found; C, 57.89; H, 5.10; N, 1486. C$_{18}$H$_{19}$BrN$_4$ requires C, 58.23; H, 5.16; N, 15.09%); δ$_H$ (DMSO-d$_6$) 2.50 (4H, m, 2×piperazinyl CH$_2$), 3.10 (4H, m, 2×piperazinyl CH$_2$), 3.67 (1H, s, CH$_2$N), 6.85 (2H, d, J 9.0 Hz, ArH), 7.04 (1H, dd, J 7.8, 4.7 Hz, 5-H), 7.31 (2H, d, J 9.0 Hz, ArH), 7.37 (1H, d, J 2.3 Hz, 2-H), 8.04 (1H, dd, J 7.8, 1.4 Hz, 4-H), 8.19 (1H, dd, J 4.7, 1.5 Hz, 6-H), and 11.45 (1H, br s, NH); m/z (CI$^+$, NH$_2$) 373/371 (M+1)$^+$.

EXAMPLE 26

(3-(4-[4-Methoxycarbonylphenyl]piperazin-1-yl]methyl-1H-pyrrolo[2,3-b]pyridine

M.p. 205°–207° C. (dec.) (PhMe); (Found: C, 67.94; H, 6.27; N, 15.70. C$_{20}$H$_{22}$N$_4$O$_2$.0.15H$_2$O requires C, 68.03; H, 6.37; N, 15.87%); δ$_H$ (DMSO-d$_6$) 2.50 (4H, m, 2×piperazinyl CH$_2$), 3.29 (4H, m, 2×piperazinyl CH$_2$), 3.68 (2H, s, CH$_2$N), 3.76 (3H, s, CO$_2$CH$_3$), 6.94 (2H, d, J 9.1 Hz, ArH), 7.05 (1H, dd, J 7.8, 4.7 Hz, 5-H), 7.38 (1H, d, J 2.1 Hz, 2-H), 7.76 (2H, d, J 9.1 Hz, ArH), 8.06 (1H, br d, J 7.8 Hz, 4-H), 8.22 (1H, dd, J 4.7, 1.5 Hz, 6-H), and 11.48 (1H, br s, NH); m/z (CI$^+$, NH$_3$) 351 (M+1)$^+$.

EXAMPLE 27

(3-(4-[4-Hydroxymethylphenyl]piperazin-1-yl)methyl-1H-pyrrolo[2,3-b]pyridine

A solution of diisobutylaluminium hydride in toluene (1.5M, 9.4 ml, 14.1 mmol) was added to a solution of (3-(4-[4-methoxycarbonylphenyl]piperazin-1-yl)methyl-1H-pyrrolo[2,3-b]pyridine (1.64 g, 4.68 mmol) in tetrahydrofuran (100 ml) and the resultant mixture stirred at room temperature for forty minutes. Methanol (3.3 ml) was added, followed by water (2.0 ml) and 2M aqueous sodium hydroxide (2.0 ml). The precipitate formed was collected, the filtrate concentrated in vacuo and the solid residue was recrystallised from methanol to afford the title compound (1.12 g, 74%), m.p. 207°–209° C. (dec.); (Found: C, 69.48; H, 7.00; N, 16.61. $C_{19}H_{22}N_4O_4 \cdot 0.3$ MeOH requires C, 69.82; H, 7.04; N, 16.87%); $\delta_H$ (DMSO-$d_6$) 2.52 (4H, m, 2×piperazinyl $CH_2$), 3.08 (4H, m, 2×piperazinyl $CH_2$), 3.68 (2H, $CH_2N$), 4.36 (2H, d, J 5.6 Hz, C$\underline{H}_2$OH), 4.92 (1H, t, J 5.6 Hz, $CH_2$O$\underline{H}$), 6.85 (2H, d, J 8.7 Hz, ArH), 7.05 (1H, dd, J 7.9, 4.7 Hz, 5-H), 7.13 (2H, d, J 8.7 Hz, ArH), 7.37 (1H, d, J 2.2 Hz, 2-H), 8.05 (1H, br d, J 7.9 Hz, 4-H), 8.19 (1H, dd, J 4.7 1.5 Hz, 6-H), and 11.47 (1H, br s, NH); m/z (CI$^+$, NH$_3$) 323 (M+1)$^+$.

EXAMPLE 28

3-(4-[5-Methyl-2-pyridyl]piperazin-1-yl)methyl-1H-pyrrolo[2,3-b]pyridine

Bromine (74 g, 24 ml, 0.46 mmol) was added dropwise with vigorous stirring to a solution of 2-amino-5-picoline (20.0 g, 0.19 mol) in 48% hydrobromic acid (300 ml) at –10° C. Sodium nitrite (32 g, 0.46 mol) in water (80 ml) was added dropwise to the orange suspension, maintaining the temperature below –5° C., and the mixture was then stirred at room temperature for 30 minutes. The mixture was recooled to 0° C., and sodium hydroxide (188 g, 4.7 mol) in water (160 ml) added dropwise. The resulting black suspension was extracted with ether (2×500 ml), the extracts combined, dried (MgSO$_4$), and evaporated to give 2-bromo-5-picoline as a tan solid (24 g, 75%); $\delta_H$ (CDCl$_3$) 2.30 (3H, s, CH$_3$), 7.38 (2H, s, 3H, 4H), 8.21 (1H, s, 6-H). This was converted in two steps, using the procedure outlined in Example 10, to the title compound, m.p. 204°–205° C., (EtOAc); (Found: C, 70.53; H, 6.86; N, 22.86. C$_{18}$H$_{21}$N$_5$ requires C, 70.33; H, 6.89; N, 22.78%); $\delta_H$ (DMSO-$d_6$) 2.12 (3H, s, ArCH$_3$), 2.47 (4H, m, 2×piperazinyl CH$_2$), 3.39 (4H, m, 2×piperazinyl CH$_2$), 3.66 (2H, s, CH$_2$N), 6.70 (1H, d, J 8.6 Hz, 4'-H), 7.36 (1H, d, J 2.3 Hz, 2-H), 5-H), 7.34 (1H, dd, J 8.6, 2.3 Hz, 4'-H), 7.36 (1H, d, J 2.3 Hz, 2-H), 7.92 (1H, d, J 2.3 Hz, 6'-H), 8.05 (1H, dd, J 7.8, 1.2 Hz, 4-H), 8.19 (1H, dd, J 4.7, 1.5 Hz, 6-H), and 11.45 (1H, br s, NH); m/z (CI$^+$, NH$_3$) 308 (M+1)$^+$.

EXAMPLE 29

3-(4-[4-Hydroxyphenyl]piperazin-1-yl)methyl-1H-pyrrolo[2,3-b]pyridine

M.p. 197°–200° C. (EtOAc); (Found: C, 68.16; H, 6.46; N, 17.34. C$_{18}$H$_{20}$N$_4$O$\cdot$0.05H$_2$O requires C, 68.12; H, 6.67; N, 17.65%); $\delta_H$ (DMSO-$d_6$) 2.93 (4H, t, J 4.3 Hz, 2×piperazinyl CH$_2$), 3.30–3.32 (4H, m, 2×piperazinyl CH$_2$), 3.67 (2H, s, ArCH$_2$N), 6.61–6.63 (2H, m, 2',6'-H), 6.73–6.76 (2H, m, 3'5'-H), 7.04 (1H, dd, J 7.8, 4.7 Hz, 5-H), 7.37 (1H, s, 2-H), 8.04 (1H, dd, J 7.8, 1.2 Hz, 4-H), 8.19 (1H, dd, J 4.7, 1.2 Hz, 6-H), 8.75 (1H, br s, OH), and 11.45 (1H, br s, NH); m/z (CI$^+$, NH$_3$) 309 (M+1)$^+$.

EXAMPLE 30

3-(4-(Benzothiophen-2-yl)piperazin-1-yl)methyl-1H-pyrrolo[2,3-b]pyridine

Step 1: 1-Benzyl-4-(benzothiophen-2-yl)piperazine

To a solution of 2-mercaptobenzothiophene (1.8 g, 10.8 mmol) in toluene under nitrogen was added N-benzylpiperazine (1.88 ml, 10.8 mmol) and the mixture heated at reflux for 1.5 h. Left to cool, concentrated in vacuo and product recrystallised from diethyl ether-hexane to yield the title compound (1.55 g), m.p. 160°–161° C.

Step 2: 1-(Benzothiophen-2-yl)piperazine hydrochloride

To a solution of 1-benzyl-4-(benzothiophen-2-yl)piperazine (1.5 g, 4.9 mmol) in anhydrous dichloromethane (20 ml) at 0° C. under nitrogen was added 1-chloroethylchloroformate (0.68 ml, 6.37 mmol). The mixture was allowed to warm to room temperature, stirred for 1 h and concentrated in vacuo. The crude residue was dissolved in methanol (10 ml) and heated to reflux for 30 minutes, left to cool and the title compound collected by filtration (0.6 g), m.p. 240° C. (dec.).

Step 3: 3-(4-(Benzothiophen-2-yl)piperazin-1-yl-1H-pyrrolo[2,3-b]pyridine

The title compound was prepared in an analogous manner to Example 6, Step 3 using 1-benzothiophen-2-yl)piperazine (180 mg, 0.83 mmol) and 3-dimethylaminomethyl-1-H-pyrrolo[2,3-b]pyridine (145 mg, 0.83 mmol). Recrystallisation from ethyl acetate-hexane afforded the title compound (155 mg, 54%), m.p. 269° C. (dec.); (Found: C, 69.10; H, 5.85; N, 16.08. C$_{20}$H$_{20}$N$_4$S requires C, 68.94; H, 5.79; N, 16.08%) $\delta_H$ (DMSO-$d_6$) 2.55 (4H, t, J 5 Hz, 2×piperazinyl CH$_2$), 3.18 (4H, t, J 5 Hz, 2×piperazinyl (CH$_2$), 3.70 (2H, s, indole-CH$_2$N), 6.26 (1H, s, 3-$\underline{H}$-benzothiophene), 7.04 (2H, m, 2×ArH), 7.19 (1H, m, ArH), 7.05 (2H, m, 2×ArH), 7.63 (1H, d, 8 Hz, ArH), 8.06 (1H, d, 8 Hz, ArH), 8.20 (1H, d, 3 Hz, ArH), and 11.46 (1H, br s, NH); m/z (CI$^+$, NH$_3$) 349 (M+1)$^+$.

EXAMPLE 31

3-(4-(benzothiophen-3-yl)piperazin-1-yl)methyl-1H-pyrrolo[2,3-b]pyridine

Step 1: 1-(Benzothiophen-3-yl)piperazine

To a solution of methyl 3-aminobenzothiophene-2-carboxylate [prepared by the method of J. R. Beck, *J. Org. Chem.* 1972, 37, 3224] (6.5 g, 31.4 mmol) in N-methylpyrrolidinone (30 ml) was added 1-methylpiperazine and the reaction mixture was heated to 178° C. for 4 h. After cooling the mixture was poured into water and the product extracted with diethyl ether (3×100 ml), the extracts were washed with water (1×100 ml) and brine (1×100 ml), combined and dried (MgSO$_4$). Concentration of the extracts yielded 3-aminobenzothiophene (5.9 g), which was used without purification. To a solution of 3-aminobenzothiophene (5 g, 32 mmol) in N-methylpyrrolidinone (50 ml) was added piperazine (8.7 g, 102 mmol) and the mixture heated to reflux under nitrogen for 14 h. Cooled and poured into water and extracted with dichloromethane (4×100 ml). The extracts were washed with brine (50 ml), combined and dried (MgSO$_4$). On concentration of the extracts a white solid came out of solution which was collected by filtration to yield the title compound (0.78 g, more product left in solution); $\delta_H$ (DMSO-$d_6$+(TFA), 3.3 (3H, m, 4×piperazinyl CH$_2$), 7.08 (1H, s, 3-H), 7.39 (2H, m, 2×ArH), 7.83 (1H, m, ArH), 7.95 (1H, m, ArH), and 9.30 (1H, br s, NH).

Step 2: 3-(4-(Benzothiophenyl-3-yl)piperazin-1-yl)methyl-1H-pyrrolo[2,3-b]pyridine The title compound was prepared in an analogus manner to Example 6, Step 3 using 1-(benzothiophenyl-3-yl)piperazine (0.5 g, 2.3 mmol) and 3-dimethylaminomethyl-1H-pyrrole[2,3-b]pyridine (0.40 g, 2.3 mmol). Recrystallisation using ethyl acetate-hexane afforded the title compound (0.18 g, 23%), m.p. 172°–173° C.; (Found: C, 68.37; H, 5.57; N, 15.90. $C_{20}H_{20}N_4S.0.1H_2O$ requires C, 68.58; H, 5.81; N, 16.00%); $\delta_H$ (DMSO-$d_6$) 2.63 (4H, br s, 2×piperazinyl $CH_2$), 3.05 (4H, br s, 2×piperazinyl $CH_2$), 3.74 (2H, s, indole-$CH_2$-N), 6.88 (1H, s, 2-benzothiophene-H), 7.06 (1H, dd, J 8, 2 Hz, ArH), 7.39 (3H, m, 3×ArH, 7.70 (1H, m, ArH), 7.88 (1H, m, ArH), 8.07 (1H, d, J 8 Hz, ArH), 8.20 (1H, m, ArH), and 11.48 (1H, br s, NH); m/z ($CI^+$, $NH_3$) 349 (M+1)$^+$.

EXAMPLE 32

(±)-3-((1H-Pyrrolo[2,3-b]pyridin-3-yl)methyl)-2,3,4,4a,5,6-hexahydro-1(H)-pyrazino[1,2-a]quinoline Using the procedure described for Example 1 replacing 1-phenylpiperazine with 2,3,4,4a,5,6-hexahydro-1(H)-pyrazino[1,2-a]quinoline [V. A. Rao et al. *Indian J. Chem.*, 7, 833 (1969) and *J. Med. Chem.*, 13, 516 (1970)] the title compound was obtained as a colourless solid, m.p. 181°–3° C. (MeOH); (Found: C, 75.27; H, 6.89; N, 17.50. $C_{20}H_{22}N_4$ requires C, 75.44; H, 6.96; N, 17.60%); $\delta_H$ (CDCl$_3$) 1.65–1.9 (2H, m, $CH_2CH_2Ar$), 1.9–2.05 and 2.2–2.35 (2H, 2m, $CH_2CH_2Ar$), 2.6–3.1 (6H, m, 3×$CH_2N$), 3.65–3.8 (3H, m, indole-$CH_2N$ and CH), 6.75 (1H, t, J 8 Hz, 9'-H), 6.8 (1H, d, J 8 Hz, 10'-H), 7.0 (1H, d, 8 Hz, 7'-H), 7.05–7.15 (2H, m, 8'-H and 5-H), 7.13 (1H, br s, 2-H), 8.13 (1H, dd, J 8, 1.5 Hz, 4-H), 8.32 (1H, dd, J 4.5, 1.5 Hz, 6-H), and 9.95 (1H, br s, NH).

EXAMPLE 33

(±)-8-Chloro-3-((1H-pyrrolo[2,3-b]pyridin-3yl)methyl)-2,3,4,4a,5,6-hexahydro-1(H)-pyrazino[1,2-a]quinoline Step 1: (±)-6-Chloro-2-((1,1-dimethylethoxycarbonylamino)methyl)-1,2,3,4-tetrahydroquinoline A solution of 6-chloroquinoline-2-carbonitrile (3.4 g, 0.018 mol) in methanol (50 ml) was shaken on a Parr hydrogenator at 55 psi $H_2$ in the presence of $PtO_2$ (0.1 g) for 18 h. The catalyst was then removed by filtration and the solvent evaporated. The residue was dissolved in dichloromethane (100 ml), cooled below −5° C. and di-tert-butyl dicarbonate (4.5 g, 0.02 mol) was added. After 2 h the solvent was evaporated and the residue triturated with hexane to afford the title compound as a colourless powder (4.3 g, 80%); $\delta_H$ (CDCl$_3$) 1.45 (9H, s, $C(CH_3)_3$), 1.6–1.75 and 1.85–1.95 (2H, 2m, $CH_2CH_2Ar$), 2.7–2.85 (2H, m, $CH_2CH_2Ar$), 3.15–3.25, 3.25–3.35, 3.35–3.45 (3H, 3m, BOCNH$CH_2CHN$), 4.88 (1H, br s, NH), 6.48 (1H, d, J 8 Hz, 8-H), 6.91–6.94 (2H, m, 5-H and 7-H).

Step 2: (±)-8-Chloro-2,3,4,4a,5,6-hexahydro-1(H)-pyrazino[1,2-a]quinolin-2-one

A solution of bromoacetyl bromide (3.2 g, 0.016 mol) in dichloromethane (10 ml) was added dropwise to a solution of (±)-6chloro-2-((1,1-dimethylethoxycarbonylamino)methyl)-1,2,3,4tetrahydroquinoline (4.3 g, 0.0145 mol) in dichloromethane (90 ml) stirring with aqueous sodium hydroxide [NaOH (0.72 g, 0.018 mol); $H_2O$ (10 ml)] cooled below 5° C. after 1 h the organic phase was separated, dried (MgSO$_4$) and evaporated to give crude bromoacetamide as a colourless solid (6 g) which was used as such.

The bromoacetamide was dissolved in dichloromethane (100 ml). TFA (15 ml) was added and the resulting homogeneous solution was stirred at room temperature for 3 h. Tlc (silica; $CH_2Cl_2$:MeOH:$NH_3$ 90:10:1) after this time showed no remaining starting material with product Rf, 0.1. The solvent and excess reagent were removed in vacuo to give the crude amine which was dissolved in DMF (100 ml), powdered potassium carbonate was then added and the resulting slurry was stirred at 80° C. under nitrogen for 24 h. Tlc (silica; $CH_2Cl_2$:MeOH:$NH_3$ 90:10:1) after this time showed product Rf, 0.5 with no remaining starting material. The insolubles were removed by filtration; the mother liquors concentrated in vacuo and the residue purified by column chromatography on silica eluting with $CH_2Cl_2$ then $CH_2Cl_2$:MeOH (95:5), to afford the title compound (1.7 g, 46%) as a buff coloured solid; $\delta_H$ (CDCl$_3$) 1.7–2.1 (2H, m, $CH_2CH_2Ar$), 2.8–3.05 (2H, m, $CH_2CH_2Ar$), 3.4–3.8 (5H, m, N$CH_2CO$ and N$CH_2CHN$), 7.12 (1H, s, 7-H), 7.15 (1H, d, J 8H, 9-H), and 7.95 (1H, d, J 8 Hz, H-10).

Step 3: (±)-8-Chloro-2,3,4,4a,5,6-hexahydro-1(H)-pyrazino[1,2-a]quinoline

Borane-tetrahydrofuran complex (1M, 6 ml) was added dropwise to a solution of 8-chloro-2,3,4,4a,5,6-hexahydro-1(H)- pyrazino[1,2-a]quinolin-2-one (0.5 g, 0.002 mol) in THF (25 ml) stirring at room temperature under nitrogen. The resulting mixture was heated at reflux for 1h, cooled in ice and 1N HCl (20 ml) was added dropwise. The mixture was heated at reflux for 1 h. The reaction mixture was then concentrated in vacuo, the residue partitioned between $CH_2Cl_2$:MeOH [1:1] (3×20 ml) and ammonia solution (20 ml). The organic phase was evaporated to give crude amine which was purified by column chromatography on silica with $CH_2Cl_2$:MeOH (9:1) as eluant to afford the title compound as a colourless oil (0.34 g, 71%); $\delta_H$ (CDCl$_3$) 1.65–1.9 (2H, m, $CH_2CH_2Ar$), 2.6–3.2 (8H, m), 3.73–3.8 (1H, m), 6.5 (1H, d, J 8 Hz, 10-H), 6.94 (1h, d, J 8 Hz, 9-H), and 6.97 (1H, s, H-7).

Step 4: (±)-8-Chloro-3-((1H-pyrrolo[2,3-b]pyridin-3-yl)methyl)2,3,4,4a,5,6-hexahydro-1(H)-pyrazino[1,2-a]quinoline Following the procedure described in Example 6, Step 3 replacing 1-(4-ethoxyphenyl)piperazine with 8-chloro-2,3,4,4a,5,6-hexahydro-1(H)-pyrazino[1,2-a]quinoline the title compound was prepared as an off-white solid (24%), m.p. 203°–5° C. (MeOH/EtOH); (Found: C, 68.29; H, 5.98; N, 15.79. $C_{20}H_{21}ClN_4$ requires C, 68.07; H, 6.00; N, 15.88%); $\delta_H$ (DMSO-$d_6$) 1.5–1.65, 1.9–2.05 and 2.08–2.15 (4H, 3m, $CH_2CH_2Ar$), 2.55–3.0 (6H, m, 3×$CH_2N$), 3.65–3.8 (3H, m, indole-$CH_2N$ and CH), 6.77 (1H, d, J 8 Hz, 9'-H), 6.9–7.1 (3H, m, 10'-H, 7'-H and 5-H), 7.36 (1H, br s, 2-H), 8.03 (1H, dd, J 8, 1.5 Hz, 4-H), 8.2 (1H, dd, J 4.5, 1.5 Hz, 6-H), and 11.5 (1H, br s, NH).

EXAMPLE 34

8-Chloro-3-((1H-pyrrolo[2,3-b]pyridin-3-yl)methyl)-2,3,4,4a,5,6-hexahydro-1(H)-pyrazino[1,2-a]quinoline Enantiomer A HPLC resolution of the enantiomers of (±)-8-chloro-3-((1H-pyrrolo[2,3-b]pyridin-3-yl)methyl)-2,3,4,4a,5,6-hexahydro-1(H)-pyrazino[1,2-a]quinoline (Example 33) was achieved using a Chiralcel OJ (250×4.6 mm id, 10 micron) column using 10% isopropanol in hexane (+0.5% diethylamine) at a flow rate of 1 ml/min. Enantiomer A was first eluting with a retention time of 15.1 min. Preparative HPLC using the above system enabled the isolation of milligram quantities of the title compound.

EXAMPLE 35

8-Chloro-3-((1H-pyrrolo[2,3-b]pyridin-3-yl)methyl-2,3,4,4a,5,6-hexahydro-1(H)-pyrazino[1,2-a]quinoline Enantiomer B HPLC resolution of the enantiomers of (±)-8-chloro-3-((1H-pyrrolo[2,3-b]pyridin-3-yl)methyl-2,3,4,4a,5,6-hexahydro-1(H)-pyrazino[1,2-a]quinoline (Example 33)

was achieved using a Chiralcel OJ (250×4.6 mm id, 10 micron) column using 10% isopropanol in hexane (+0.5% diethylamine) at a flow rate of 1 ml/min. Enantiomer B was second eluting with a retention time of 21.6 min. Preparative HPLC using the above system enabled the isolation of 5 milligram quantities of the title compound.

EXAMPLE 36

(±)-8-Chloro-3-((1H-pyrrolo[2,3-b]pyridin-3-yl)methyl-2, 3,4,4a,5,6-hexahydro-1(H)-pyrazino[1,2-c]-1,4-benzoxazine Step 1: (±)-8-Chloro-2,3,4,4a,5,6-hexahydro-1(H)-pyrazine [2,1-c]-1,4-benzoxazine Following the procedure of Gupta et al. *Indian J. Chem.* 18, 462–7 (1975) replacing 2-nitrophenol with 5-chloro-2-nitrophenol the title compound was obtained as a colourless oil; $\delta_H$ (CDCl$_3$) 2.45 (1H, dd, J 12, 12 Hz, CH), 2.6 (1H, ddd, J, 12, 12, 3 Hz, CH), 2.8–3.15 (4H, m, 4×CH), 3.5 (1H, dd, J 12, 2 Hz, CH), 3.9 (1H, dd, J 9, 9 Hz, CH), 4.08 (1H, dd, J 12, 2 Hz, CH), 6.6 (1H, d, J 8 Hz, 10'-H), 6.7 (1H, d, J 2 Hz, 7'-H, and 6.72 (1H, dd, J 8, 2 Hz, 9'-H).

Step 2: (±)-8-Chloro-3-((1H-pyrrolo[2,3-b]pyridin-3-yl)methyl)-2,3,4,4a,5,6-hexahydro-1(H)-pyrazino[2,1-c]-1,4-benzoxazine Following the procedure described in Example 6, Step 3 replacing 1-(4-ethoxyphenyl)piperazine with (±)-8-Chloro-2,3,4,4a,5,6-hexahydro-1(H)-pyrazino[2,1-c]-1,4-benzoxazine the title compound was obtained as a colourless solid, m.p.>200° C. (MeOH); (Found: C, 63.98; H, 5.37; N, 15.49. C$_{19}$H$_{19}$ClN$_4$O requires C, 64.31; H, 5.39; N, 15.79%); $\delta_H$ (DMSO-d$_6$) 1.73 (1H, dd, J 11, 2 Hz, CH), 2.14 (1H, dd, J 11, 1.5 Hz, CH), 2.55 (1H, dd, J 11, 2 Hz, CH), 2.75–3.0 (3H, m, 3×CH), 3.6–3.7 (3H, m, 3×CH), 3.86 (1H, t, J 9 Hz, CH), 4.21 (1H, dd, J 10, 3 Hz, CH), 6.72 (1H, s, 7'-H), 6.75–6.85 (2H, m, 10'-H and 9'-H), 7.04 (1H, dd, J 8, 4.5 Hz, 5-H), 7.38 (1H, br s, 2-H), 8.03 (1H, dd, J 8, 2 Hz, 4-H), 8.2 (1H, dd, J 4.5, 2 Hz, 6-H), and 11.5 (1H, br s, NH); m/z (CI$^+$, NH$_3$) 355, 357 (M+1)$^+$.

EXAMPLE 37

3-(4-[4-Methoxymethylphenyl]piperazin-1-yl)methyl-1H-pyrrolo[2,3-b]pyridine

Step 1: 1-(tert-Butoxycarbonyl)-4-(4-trifluoromethanesulfonyloxyphenyl)piperazine Triethylamine (0.77 ml, 5.52 mmol) was added to a suspension of 1-(tert-butoxycarbonyl)-4-(4-hydroxyphenyl)piperazine (1.39 g, 4.99 mmol) in dichloromethane and the resulting solution cooled to 0° C. Trifluoromethanesulfonic anhydride (0.92 ml, 5.47 mmol) was added and the reaction mixture stirred at 0° C. for 1 hour under nitrogen. The mixture was concentrated in vacuo to a dark brown oil which was redissolved in dichloromethane (50 ml) and washed with 1M hydrochloric acid (50 ml), 1M sodium hydroxide solution (50 ml) and brine (50 ml). The organic phase was dried (MgSO$_4$) and concentrated in vacuo to give the title compound (1.93 g, 94%), as a pale amber oil which crystallised on standing; $\delta_H$ (CDCl$_3$) 1.48 (9H, s, C(CH$_3$)$_3$), 3.16 (4H, m, 2×piperazinyl CH$_2$), 3.59 (4H, m, 2×piperazinyl CH$_2$), 6.91 (2H, m, ArH), and 7.16 (2H, m, ArH).

Step 2: 1-(tert-Butoxycarbonyl)-4-(4-methoxycarbonylphenyl)piperazine

A mixture of 1-(tert-butoxycarbonyl)-4-(4-trifluoromethanesulfonyloxyphenyl)piperazine (1.92 g, 4.68 mmol), palladium (II) acetate (52.5 mg, 0.23 mmol), 1,1'-bis(diphenylphosphino)ferrocene (325.0 mg, 0.59 mmol), triethylamine (1.3 ml, 9.33 mmol), methanol (8 ml) and dimethylformamide (20 ml) was purged with carbon moxoxide for 15 minutes, sealed under a balloon of carbon monoxide and stirred at 60° C. overnight (18 hours). The reaction mixture was allowed to cool, concentrated in vacuo to a small volume and the residue triturated with ethyl acetate. The solid was collected, washed with ethyl acetate and dried to give the title compound (0.659 g, 44%), as a pale cream solid. Evaporation of the ethyl acetate mother liquors and purification of the residue by flash chromatography (eluting with 5% to 10% ethyl acetate in dichloromethane) gave more of the title compound (0.492 g, 33%); $\delta_H$ (CDCl$_3$) 1.49 (9H, s, C(CH$_3$)$_3$), 3.31 (4H, m, 2×piperazinyl CH$_2$), 3.60 (4H, m, 2×piperazinyl CH$_2$), 3.87 (3H, s, CO$_2$CH$_3$), 6.89 (2H, m, ArH), and 7.94 (2H, m, ArH).

Step 3: 1-(tert-Butoxycarbonyl)-4-(4-hydroxymethylphenyl)piperazine

Diisobutylaluminium hydride in toluene (1.5M, 15 ml, 22.5 mmol) was added dropwise to a solution of 1-(tert-butoxycarbonyl)-4-(4-methoxycarbonylphenyl)piperazine (2.90 g, 9.05 mmol) in THF (116 ml) at 0° C. The mixture was stirred at 0° C. for 2 hours then allowed to warm to room temperature. The solution was recooled to −4° C. and the reaction quenched by the addition of methanol (6 ml), water 3 ml) and finally 2M sodium hydroxide (3 ml). The mixture was allowed to warm to room temperature, the precipitated aluminium salts collected under suction and washed with dichloromethane. The filtrate was concentrated in vacuo and the residue purified by flash chromatography, eluting with dichloromethane/ethyl acetate, to give the title compound (2.30 g, 74%); $\delta_H$ (CDCl$_3$) 1.48 (9H, s, C(CH$_3$)$_3$), 1.60 (1H, v br, CH$_2$OH), 3.13 (4H, m, 2×piperazinyl CH$_3$), 3.58 (4H, m, 2×piperazinyl CH$_2$), 4.61 (2H, s, CH$_2$OH), 6.92 (2H, m, ArH), and 7.29 (2H, m, ArH).

Step 4: 1-(tert-Butoxycarbonyl)-4-(4-methoxymethylphenyl)piperazine

Sodium hydride (80% dispersion in oil; 0.10 g, 3.3 mmol) was added to a solution of (1-tert-butoxycarbonyl)-4-(4-hydroxymethylphenyl)piperazine (0.80 g, 2.74 mmol) in THF (10 ml) at 0° C. The mixture was stirred at 0° C. for 90 minutes, allowed to warm to room temperature and stirred for a further 30 minutes. The mixture was recooled to 0° C., methyl iodide (0.20 ml, 3.2 mmol) added dropwise and the mixture stirred at room temperature overnight. TLC indicated that starting material remained unreacted. A further portion of sodium hydride (0.04 g, 1.3 mmol) was added, the reaction mixture stirred at room temperature for one hour, methyl iodide (0.17 ml, 2.78 mmol) was added and the mixture stirred overnight. The reaction mixture was poured into water (100 ml) and extracted with ethyl acetate (2×50 ml). The extracts were washed with brine (50 ml), combined, dried (MgSO$_4$) and concentrated in vacuo. The residue was purified by flash chromatography eluting with ethyl acetate/petrol (60°–80°) to give the title compound (0.62 g, 74%); $\delta_H$ (DMSO-d$_6$) 1.42 (9H, s, C(CH$_3$)$_3$), 3.08 (4H, m, 2×piperazinyl CH$_2$), 3.22 (3H, s, CH$_2$OCH$_3$), 3.45 (4H, m, 2×piperazinyl CH$_2$), 4.28 (2H, s, ArCH$_2$OCH$_3$), 6.92 (2H, m, ArH), and 7.17 (2H, m, ArH).

Step 5: 1-(4-Methoxymethylphenyl)piperazine

A solution of hydrogen chloride in ether (10 ml) was added to a solution of 1-(tert-butoxycarbonyl)-4-(4-methoxymethylphenyl)piperazine (0.62 g, 2.02 mmol) in ethyl acetate (10 ml) and the resulting mixture stirred at room temperature for 15 minutes. The mixture was poured into saturated aqueous potassium carbonate (200 ml) and extracted with dichloromethane (2×100 ml). The extracts were washed with brine (100 ml), combined, dried (MgSO$_4$) and concentrated. The residue was purified by flash chromatography, eluting with 90:8:1 then 60:8:1 dichloromethane/methanol/ammonia, to give the title compound (0.26 g, 62%), as a pale brown oil; $\delta_H$ (CDCl$_3$) 3.03 (4H, m, 2×piperazinyl CH$_2$), 3.14 (4H, m, 2×piperazinyl CH$_2$), 3.34 (3H, s, CH$_2$OC$\underline{H}_3$), 4.37 (2H, S, ArC$\underline{H}_2$OCH$_2$), 6.90 (2H, m, ArH), and 7.23 (2H, m, ArH).

Step 6: 3-(4-[4-Methoxymethylphenyl]piperazin-1-yl)methyl-1H-pyrrolo[2,3-b]pyridine 1-(4-Methoxymethylphenyl)piperazine was converted into the title compound by the method outline in Example 6, Step 3.

M.p. 161.5°–163° C. (MeOH); (Found: C, 71.46; H, 7.07; N, 16.09. C$_{20}$H$_{24}$N$_4$O.0.06 C$_7$H$_8$ requires C, 71.72; H, 7.22; N, 16.38%); $\delta_H$ (DMSO-d$_6$) 2.52 (4H, m, 2×piperazinyl CH$_2$), 3.10 (4H, m, 2×piperazinyl CH$_2$), 3.21 (3H, s, CH$_2$OC$\underline{H}_3$), 3.68 (2H, s, CH$_2$N), 4.26 (2H, s, ArC$\underline{H}_2$OCH$_2$), 6.87 (2H, d, J 8.6 Hz, ArH), 7.04 (1H, dd, J 7.8, 4.6 Hz, 5-H), 7.13 (2H, d, J 8.6 Hz, ArH), 7.37 (1H, br s, 2-H), 8.05 (1H, br d, J 7.8 Hz, 4-H), 8.19 (1H, dd, J 4.6, 1.4 Hz, 6-H), and 11.47 (1H, br s, NH); m/z (CI$^+$, NH$_3$) 337 (M+1).

EXAMPLE 38

3-(4-[4-Dimethylaminomethylphenyl]piperazin-1-yl)methyl-1H-pyrrolo[2,3-b]pyridine Step 1: 1-(4-Dimethylcarboxamidophenyl)piperazine A mixture of 1-(tert-butoxycarbonyl)-4-(4-trifluoromethanesulfonyloxyphenyl)piperazine (7.4 g, 18 mmol), palladium(II) acetate (198 mg, 0.88 mmol), 1,1'bis(diphenylphosphino)ferrocene (1.28 g, 2.25 mmol), triethylamine (17.6 ml, 126 mmol), dimethylamine hydrochloride (7.3 g, 90 mmol) and dimethylformamide (75 ml) was purged with carbon monoxide for 15 minutes, sealed under a balloon of carbon monoxide and stirred at 60° C. overnight (20 hours). The reaction was cooled and concentrated in vacuo to a small volume. Water (50 ml) and ethyl acetate (50 ml) were added and the phases were separated. The aqueous was extracted with ethyl acetate (2×50 ml). The combined organics were washed with water (20 ml) and brine (20 ml), dried (MgSO$_4$) and evaporated in vacuo to give a purple residue. The crude product was chromatographed on silica eluting with 2% methanol/dichloromethane. The amine was deprotected by dissolving the compound in ethyl acetate and treatment with ethereal hydrogen chloride. The gum obtained was partitioned between hydrochloric acid (0.5M) and ether, the phases were separated and the aqueous washed again with ether. The aqueous was basified with sodium hydroxide (10M) and extracted with n-butanol (4×50 ml). The extracts were dried (Na$_2$SO$_4$) and evaporated in vacuo to give the title compound as a brown gum (0.8 g, 19%), $\delta_H$ (CDCl$_3$) 2.98–3.14 (8H, m, N(C$\underline{H}_3$)$_2$ and piperazinyl CH$_2$), 3.18–3.30 (4H, m, 2×piperazinyl CH$_2$), 3.56–3.65 (2H, m, piperazinyl CH$_2$), 6.89 (2H, d, J 12.5 Hz, ArH), and 7.40 (2H, d, J 12.5 Hz, ArH).

Step 2: 3-(4-[4-Dimethylcarboxamidophenyl]piperazin-1-yl)methyl-1H-pyrrolo[2,3-b]pyridine 1-(4-Dimethylcarboxamidophenyl)piperazine was converted into the title compound by the method outline in Example 6, Step 3; m.p. 217°–219° C. (MeOH).

Step 3: 3-(4-[4-Dimethylaminomethylphenyl]piperazin-1-yl)methyl-1H-pyrrolo[2,3-b]pyridine Lithium aluminium hydride (1M solution in THF, 2.7 ml, 2.7 mmol) was carefully added to a suspension of 3-(4-[4-dimethylcarboxamidophenyl]piperazin-1-yl)methyl-1H-pyrrolo[2,3-b]pyridine (650 mg, 1.79 mmol) in tetrahydrofuran (30 ml) under a nitrogen atmosphere and the resultant solution was heated at reflux for 2 hours.

The mixture was cooled to room temperature and treated with water (0.1 ml), sodium hydroxide (4N, 0.1 ml) and water (0.3 ml). The mixture was filtered through celite® and the filter cake was washed with tetrahydrofuran. The filtrate was evaporated in vacuo and the residue triturated with ether. Recrystallisation from ethyl acetate gave the title compound as an off white solid (228 mg, 36%), m.p. 163°–165° C.; (Found: C, 71.72; H, 7.90; N, 20.02. C$_{21}$H$_{27}$N$_5$.0.2 (H$_2$O) requires C, 71.80; H, 7.81; N, 19.93%); $\delta_H$ (DMSO-d$_6$) 2.08 (6H, s, N(CH$_3$)$_2$), 2.49–2.53 (4H, m, 2×piperazinyl CH$_2$), 3.07 (4H, m, 2×piperazinyl CH$_2$), 3.24 (2H, s, ArC$\underline{H}_2$N(CH$_3$)$_2$), 3.67 (2H, s, ArCH$_2$N), 6.84 (2H, d, J 8.6 Hz, 2×ArH), 7.02–7.09 (3H, m, ArH), 7.37 (1H, d, J 2.1 Hz, 2-H), 8.04 (1H, dd, J 7.8, 1.2 Hz, 4-H), 8.18 (1H, dd, J 4.6, 1.5 Hz, 6-H), and 11.47 (1H, br s, NH); m/z (CI$^+$, NH$_3$) 350 (M+1)$^+$.

EXAMPLE 39

3-(1,2,3,4,10,10a-Hexahydropyrazino[1,2-a]indol-2-yl)methyl-1H-pyrrolo[2,3-b]pyridine Step 1: 1,2,3,4,10,10a-Hexahydropyrazino[1,2-a]indole Palladium on charcoal (10%, 660 mg) was carefully added to a solution of 2-benzyl-1,2,3,4-tetrahydropyrazino[1,2-a]indole hydrochloride (4.2 g, 140 mmol) (prepared using the method of Freed, U.S. Pat. No. 3,317,524) in methanol (200 ml) under a nitrogen atmosphere and the mixture was hydrogenated at 45 psi, 50° C. for 3.5 hours after which time the hydrogen uptake had ceased. The catalyst was removed by filtration and the filtrate concentrated in vacuo to about 50 ml. Dry ether (100 ml) was added, the precipitated pink solid was collected by filtration and dried in vacuo. This hydrochloride salt was partitioned between sodium hydroxide solution (2N, 100 ml) and ethyl acetate (100 ml), the phases were separated and the aqueous extracted with ethyl acetate (100 ml and 50 ml). The combined organics were washed with brine (50 ml), dried (Na$_2$SO$_4$) and evaporated in vacuo to give a red oil. The oil was purified by column chromatography on silica eluting with 10% methanol/dichloromethane to give 1,2,3,4-tetrahydropyrazine [1,2-a]indole (1.48 g, 61%) and 1,2,3,4,10,10a-hexahydropyrazino[1,2,-a]indole (280 mg, 11%); $\delta_H$ (CDCl$_3$), 2.53–2.60 (1H, m, aliphatic CH), 2.78–31.7 (6H, m, 3×aliphatic CH$_2$), 3.47–3.71 (2H, m, aliphatic CH$_2$), 6.45 (1H, t, J 7.7 Hz, ArH), 6.64–6.68 (1H, m, ArH), and 7.05–7.09 (2H, m, ArH).

Step 2: 3-(1,2,3,4,10,10a-Hexahydropyrazino[1,2-a]indol-2-yl)methyl-1H-pyrrolo[2,3-b]pyridine Following the procedure described in Example 6, Step 3 replacing 1-(4-ethoxyphenyl)piperazine with 1,2,3,4,10,10a-hexahydropyrazino[1,2-a]indole the title compound was obtained, m.p. 197°–198° C. (EtOAc); (Found: C, 74.53; H, 6.77; N, 17.86. C$_{19}$H$_{20}$N$_4$.0.05 (CH$_3$CO$_2$C$_2$H$_5$) requires C, 74.68; H, 6.66; N, 18.14%); $\delta_H$ (DMSO-d$_6$) 1.91–1.98 (1H, m, 1×aliphatic H), 2.05 (1H, dt, J 3.0, 11.3 Hz, 1×aliphatic H), 2.43 (1H, m, 1×aliphatic H), 2.76–2.90 (4H, m, 4×aliphatic H), 3.42–3.69 (4H, m, 4×aliphatic H), 6.43–6.53 (2H, m, ArH), 6.92–7.05 (3H, m, ArH), 7.34 (1H, d, J 2.2 Hz, 2-H), 8.03 (1H, dd, J 7.8, 1.3 Hz, 4-H), 8.18 (1H, dd, J 4.6, 1.4 Hz, 6-H), and 11.47 (1H, br s, NH); m/z (CI$^+$, NH$_3$) 305 (M+1)$^+$.

What is claimed is:

1. A method for the treatment and/or prevention of schizophrenia, which comprises administering to a patient in need of such treatment an effective amount of a compound of formula I, or a pharmaceutically acceptable salt thereof:

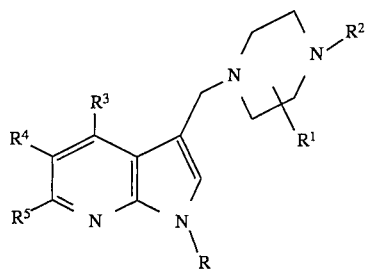

(I)

wherein

R represents hydrogen or $C_{1-6}$ alkyl;

$R^1$ represents hydrogen, halogen, or an optionally substituted $C_{1-6}$ alkyl, $C_{1-6}$ alkoxy, $C_{2-6}$ alkenyl, $C_{2-6}$ alkynyl, aryl which is selected from the group consisting of phenyl and naphthyl, aryl($C_{1-6}$)alkyl, aryloxy ($C_{1-6}$)alkyl, aryl($c_{1-6}$)alkoxy, aryl($C_{2-6}$)alkenyl, aryl($C_{2-6}$)alkynyl group;

$R^2$ represents an optionally substituted $C_{1-6}$ alkyl, $C_{1-6}$alkoxy, $C_{2-6}$ alkenyl, $C_{2-6}$ alkynyl, aryl, aryl ($C_{1-6}$)alkyl, aryloxy($C_{1-6}$)alkyl, aryl($C_{1-6}$)alkoxy, aryl($C_{2-6}$)alkenyl, aryl($C_{2-6}$)alkynyl, $C_{3-7}$ heterocycloalkyl($C_{1-6}$)alkyl, wherein heterocycloalkyl is selected from the group consisting of azetidinyl, pyrrolidyl, piperidyl, piperazinyl, morpholinyl and tetrahydrofuryl; heteroaryl, selected from the group consisting of pyridyl, quinolyl, isoquinolyl, pyrimidinyl, pyrazinyl, pyranyl, furyl, benzofuryl, dibenzofurly, thienyl, benzthienyl, indolyl, indazolyl, imidazolyl, benzimidazolyl, oxathiazolyl and thiadiazolyl; heteroaryl($C_{2-6}$)alkenyl or heteroaryl($C_{2-6}$)alkynyl group;

$R^3$, $R^4$ and $R^5$ independently represent hydrogen, halogen, cyano, trifluoromethyl, nitro, amino, $C_{1-6}$alkylamino, di($C_{1-6}$)alkylamino, $C_{1-6}$alkyl, $C_{1-6}$alkoxy, aryl($C_{1-6}$)alkoxy, and $C_{2-6}$alkylcarbonyl.

2. The method as claimed in claim 1 wherein $R^1$ is other than hydrogen.

3. The method as claimed in claim 1 wherein $R^1$ represents hydrogen, or an optionally substituted $C_{1-6}$ alkyl, $C_{1-6}$ alkoxy, $C_{2-6}$ alkenyl, $C_{2-6}$ alkynyl, aryl, aryl($C_{1-6}$)alkyl, aryloxy($C_{1-6}$)alkyl, aryl($C_{1-6}$)alkoxy, aryl($C_{1-6}$)alkenyl, aryl($C_{2-6}$)alkynyl, $C_{3-7}$ heterocycloalkyl($C_{1-6}$)alkyl, heteroaryl, heteroaryl($C_{1-6}$)alkyl, heteroaryl($C_{2-6}$)alkenyl or heteroaryl($C_{2-6}$)alkynyl group; and R, $R^2$, $R^3$, $R^4$ and $R^5$ are as defined in claim 1.

4. The method as claimed in claim 1 wherein the compound administered is represented by formula IIA, and pharmaceutically acceptable salts thereof:

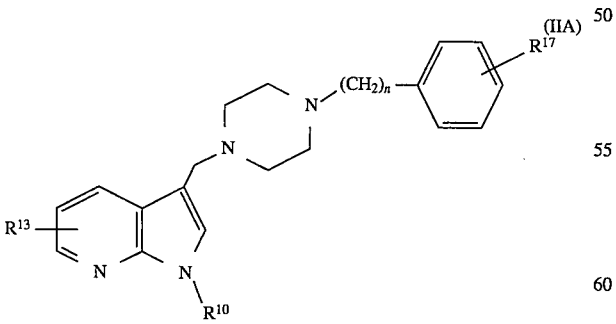

(IIA)

wherein n is zero, 1, 2 or 3;

$R^{10}$ represents hydrogen or methyl;

$R^{13}$ represents hydrogen, halogen, cyano, nitro, trifluoromethyl, amino, $C_{1-6}$ alkylamino, di($C_{1-6}$)alkylamino, $C_{1-6}$ alkyl, $C_{1-6}$ alkoxy, aryl($C_{1-6}$)alkoxy or $C_{2-6}$ alkylcarbonyl; and $R^{17}$ represents hydrogen, $C_{1-6}$ alkyl, halogen, trifluoromethyl, hydroxy, hydroxy($C_{1-6}$)alkyl, $C_{1-6}$ alkoxy, aryl($C_{1-6}$)alkoxy, $C_{1-6}$ alkoxy($C_{1-6}$)alkyl, carboxy, $C_{2-6}$ alkoxycarbonyl, $C_{2-6}$ alkylcarbonyl, cyano, nitro, amino, $C_{1-6}$ alkylamino, di($C_{1-6}$)alkylamino, amino($C_{1-6}$)alkyl, $C_{1-6}$ alkylamino($C_{1-6}$)alkyl or di($C_{1-6}$)alkylamino($C_{1-6}$)alkyl.

5. A compound of formula IIB, or a pharmaceutically acceptable salt thereof:

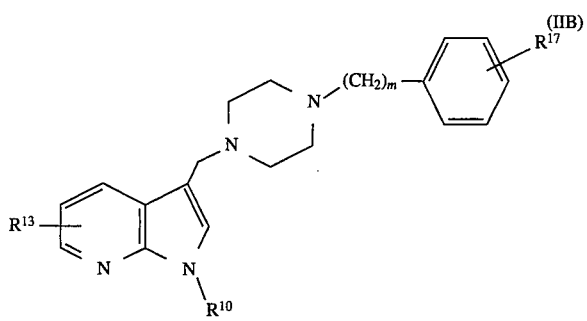

(IIB)

wherein m is 1, 2, or 3; and $R^{10}$ represents hydrogen or methyl;

$R^{13}$ represents hydrogen, halogen, cyano, nitro, trifluoromethyl, amino, $C_{1-6}$ alkylamino, di($C_{1-6}$)alkylamino, $C_{1-6}$ alkyl, $C_{1-6}$ alkoxy, aryl($C_{1-6}$)alkoxy or $C_{2-6}$ alkylcarbonyl; and $R^{17}$ represents hydrogen, $C_{1-6}$ alkyl, halogen, trifluoromethyl, hydroxy, hydroxy($C_{1-6}$)alkyl, $C_{1-6}$ alkoxy, aryl($C_{1-6}$)alkoxy, $C_{1-6}$ alkoxy($C_{1-6}$)alkyl, carboxy, $C_{2-6}$ alkoxycarbonyl, $C_{2-6}$ alkylcarbonyl, cyano, nitro, amino, $C_{1-6}$ alkylamino, di($C_{1-6}$) alkylamino, amino ($C_{1-6}$)alkyl, $C_{1-6}$ alkylamino($C_{1-6}$)alkyl or di($C_{1-6}$)alkylamino($C_{1-6}$)alkyl.

6. A compound of formula IIC, or a pharmaceutically acceptable salt thereof.

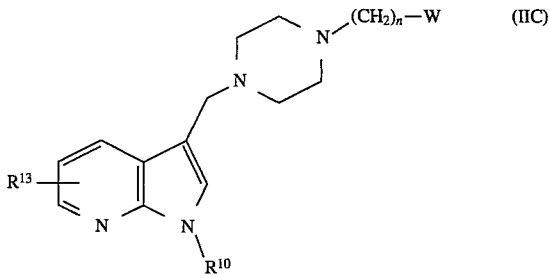

(IIC)

wherein n is zero, 1, 2 or 3;

$R^{10}$ represents hydrogen or methyl;

$R^{13}$ represents hydrogen, halogen, cyano, nitro, trifluoromethyl, amino, $C_{1-6}$ alkylamino, di($C_{1-6}$)alkylamino, $C_{1-6}$ alkyl, $C_{1-6}$ alkoxy, aryl($C_{1-6}$)alkoxy or $C_{2-6}$ alkylcarbonyl;

W represents a group of formula (i), (ii), (iii) or (iv):

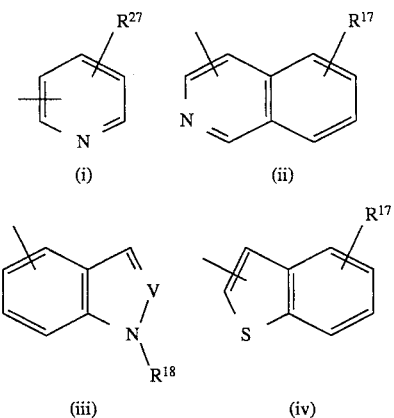

in which

V represents nitrogen or CH:

R$^{17}$ represents hydrogen, C$_{1-6}$ alkyl, halogen, trifluoromethyl, hydroxy, hydroxy(C$_{1-6}$)alkyl, C$_{1-6}$ alkoxy, aryl(C$_{1-6}$)alkoxy, C$_{1-6}$ alkoxy(C$_{1-6}$)alkyl, carboxy, C$_{2-6}$ alkoxycarbonyl, C$_{2-6}$ alkylcarbonyl, cyano, nitro, amino, C$_{1-6}$ alkylamino, di(C$_{1-6}$)alkylamino (C$_{1-6}$)alkyl, C$_{1-6}$ alkylamino(C$_{1-6}$)alkyl or di(C$_{1-6}$)alkylamino(C$_{1-6}$)alkyl;

R$^{18}$ represents hydrogen or methyl; and

R$^{27}$ represents C$_{1-6}$ alkyl, halogen, trifluoromethyl, C$_{1-6}$ alkoxy, cyano, nitro, amino, C$_{1-6}$ alkylamino or di(C$_{1-6}$)alkylamino.

7. The method as claimed in claim 4 wherein the compound administer is represented by formula IIE: or a pharmaceutically acceptable salt thereof:

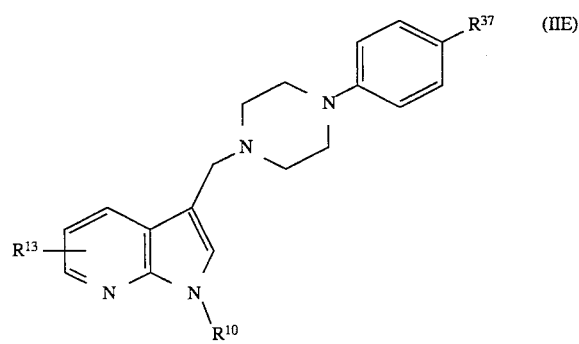

wherein

R$^{13}$ is as defined in claim 4; and

R$^{37}$ represents fluoro, bromo, iodo or trifluoromethyl.

8. The method as claimed in claim 4 wherein the compound administered is selected from:
3-(4-phenylpiperazin-1-yl)methyl-1H-pyrrolo[2,3-b]pyridine;
3-[4-(4-methoxyphenyl)piperazin-1-yl]methyl-1H-pyrrolo[2,3-b]pyridine;
3-(4-benzylpiperazin-1-yl)methyl-1H-pyrrolo[2,3-b]pyridine; and
3-[4-(4-ethylphenyl)piperazin-1-yl]methyl-1H-pyrrolo[2,3-b]pyridine;
and pharmaceutically acceptable salts thereof.

9. The method as claimed in claim 4 wherein the compound administered is selected from:
3-[4-(4-ethoxyphenyl)piperazin-1-yl]methyl-1H-pyrrolo[2,3-b]pyridine;
3-[4-(4-dimethylaminophenyl)piperazin-1-yl]methyl-1H-pyrrolo[2,3-b]pyridine;
3-[4-(3,4-dichlorophenyl)piperazin-1-yl]methyl-1H-pyrrolo[2,3-b]pyridine;
3-[4-(4-methoxyphenyl)piperazin-1-yl]methyl-1-methyl-1H-pyrrolo[2,3-b]pyridine;
3-[4-(4-iodophenyl)piperazin-1-yl]methyl-1H-pyrrolo[2,3-b]pyridine;
3-[4-(4-trifluoromethylphenyl)piperazin-1-yl]methyl-1H-pyrrolo[2,3-b]pyridine; and
3-[4-(4-methylphenyl)piperazin-1-yl]methyl-1H-pyrrolo[2,3-b]pyridine;
and pharmaceutically acceptable salts thereof.

10. The method as claimed in claim 4 wherein the compound administered is selected from:
3-[4-(4-fluorophenyl)piperazin-1-yl]methyl-1H-pyrrolo[2,3-b]pyridine;
3-[4-(4-ethoxycarbonylphenyl)piperazin-1yl]methyl-1H-pyrrolo[2,3-b]pyridine;
3-[4-(4-carboxyphenyl)piperazin-1-yl]methyl-1H-pyrrolo[2,3-b]pyridine;
3-[4-(3-methylphenyl)piperazin-1-yl]methyl-1H-pyrrolo[2,3-b]pyridine;
3-[4-(2-methylphenyl)piperazin-1-yl]methyl-1H-pyrrolo[2,3-b]pyridine;
3-[4-(3,4-methylenedioxyphenyl)piperazin-1-yl]methyl-1H-pyrrolo[2,3-b]pyridine;
3-[4-(4-bromophenyl)piperazin-1-yl]methyl-1H-pyrrolo[2,3-b]pyridine;
3-[4-(4-methoxycarbonylphenyl)piperazin-1-yl]methyl-1H-pyrrolo[2,3-b]pyridine;
3-[4-(4-hydroxymethylphenyl)piperazin-1-yl]methyl-1H-pyrrolo[2,3-b]pyridine;
3-[4-(4-hydroxyphenyl)piperazin-1-yl]methyl-1H-pyrrolo[2,3-b]pyridine;
3-[4-(4-methoxymethylphenyl)piperazin-1-yl]methyl-1H-pyrrolo[2,3-b]pyridine; and
3-[4-(4-dimethylaminomethylphenyl)piperazin-1-yl]methyl-1H-pyrrolo[2,3-b]pyridine;
and pharmaceutically acceptable salts thereof.

11. The compound as claimed in claim 6 selected from:
3-[4-(5-chloropyrid-2-yl)piperazin-1-yl]methyl-1H-pyrrolo[2,3-b]pyridine;
3-[4-(3-isoquinolyl)piperazin-1-yl]methyl-1H-pyrrolo[2,3-b]pyridine;
3-[4-(5-indolyl)piperazin-1-yl]methyl-1H-pyrrolo[2,3-b]pyridine;
3-[4-(1-methylindol-5-yl)piperazin-1yl]methyl-1H-pyrrolo[2,3-b]pyridine;
3-[4-(indazol-5-yl)piperazin-1-yl]methyl-1H-pyrrolo[2,3-b]pyridine;
3-[4-(5-methylpyrid-2-yl)piperazin-1-yl]methyl-1H-pyrrolo[2,3-b]pyridine;
3-[4-(benzothiophen-2-yl)piperazin-1-yl]methyl-1H-pyrrolo[2,3-b]pyridine;
3-[4-(benzothiophen-3-yl)piperazin-1-yl]methyl-1H-pyrrolo[2,3-b]pyridine;
and pharmaceutically acceptable salt thereof.

12. The compound as claimed in claim 5 which is
3-[4-(2-phenoxyethyl)piperazin-1-yl]methyl-1H-pyrrolo[2,3-b]pyridine
or a pharmaceutically acceptable salt thereof.

13. A pharmaceutical composition comprising an therapeutically effective amount of a compound according to claim 5 in association with a pharmaceutically acceptable carrier.

14. A pharmaceutical composition comprising an therapeutically effective amount of a compound according to claim 6 in association with a pharmaceutically acceptable carrier.

15. A pharmaceutical composition comprising an therapeutically effective amount of a compound according to claim 8 in association with a pharmaceutically acceptable carrier.

16. A pharmaceutical composition comprising an therapeutically effective amount of a compound according to claim 9 in association with a pharmaceutically acceptable carrier.

17. A pharmaceutical composition comprising an therapeutically effective amount of a compound according to claim 10 in association with a pharmaceutically acceptable carrier.

18. A method for the treatment and/or prevention of schizophrenia, which comprises administering to a patient in need of such treatment an therapeutically effective amount of a compound according to claim 5.

19. A method for the treatment and/or prevention of schizophrenia, which comprises administering to a patient in need of such treatment an therapeutically effective amount of a compound according to claim 6.

20. A method for the treatment and/or prevention of schizophrenia, which comprises administering to a patient in need of such treatment an effective amount of a compound of structural formula IIE:

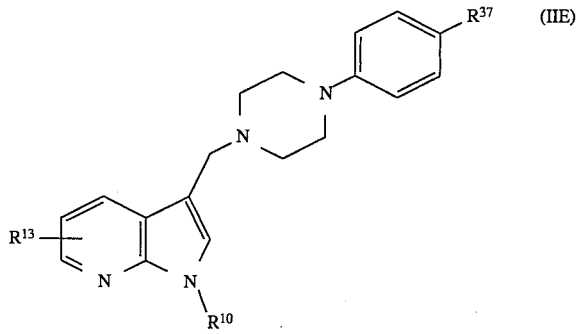

wherein $R^{13}$ represents hydrogen, halogen, cyano, nitro, trifluoromethyl, amino, $C_{1-6}$ alkylamino, di $(C_{1-6})$ alkylamino, $C_{1-6}$ alkyl, $C_{1-6}$ alkoxy, aryl $(C_{1-6})$ alkoxy or $C_{2-6}$ alkylcarbonyl; and $R^{37}$ represents fluoro, chloro, bromo, iodo, or trifluoromethyl.

21. A method for the treatment and/or prevention of schizophrenia, which comprises administering to a patient in need of such treatment an effective amount of a compound according to claim 8.

22. A method for the treatment and/or prevention of schizophrenia, which comprises administering to a patient in need of such treatment an effective amount of a compound according to claim 9.

23. A method for the treatment and/or prevention of schizophrenia, which comprises administering to a patient in need of such treatment an effective amount of a compound according to claim 10.

24. A method according to claim 1 of treating the symptoms of schizophrenia without causing sedation or extrapyramidal side-effects.

25. A method according to claim 24 for alleviating the positive symptoms of schizophrenia.

26. A method according to claim 24 for alleviating the negative symptoms of schizophrenia.

27. A method according to claim 24 in which the compound of formula I has a human dopamine $D_4$ receptor subtype binding affinity $(K_i)$ of 10 nM or less.

28. A method according to claim 24 in which the compound of formula I has at least a 50-fold selective affinity for the human dopamine $D_4$ receptor subtype with respect to the $D_2$ subtype.

29. The method according to claim 24 wherein, in the compound of formula I, R, $R^1$, $R^3$, $R^4$ and $R^5$ each represents hydrogen, and $R^2$ represents an optionally substituted phenyl group.

30. The method according to claim 29 wherein $R^2$ represents chlorophenyl.

* * * * *